(12) United States Patent
Stahmann et al.

(10) Patent No.: US 9,764,148 B2
(45) Date of Patent: *Sep. 19, 2017

(54) ENERGY ADAPTIVE COMMUNICATION FOR MEDICAL DEVICES

(71) Applicant: Cardiac Pacemakers, Inc., St. Paul, MN (US)

(72) Inventors: Jeffrey E. Stahmann, Ramsey, MN (US); Paul Huelskamp, St. Paul, MN (US); Michael J. Kane, Roseville, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/239,418

(22) Filed: Aug. 17, 2016

(65) Prior Publication Data

US 2016/0354613 A1    Dec. 8, 2016

Related U.S. Application Data

(63) Continuation of application No. 14/836,247, filed on Aug. 26, 2015, now Pat. No. 9,446,253.
(Continued)

(51) Int. Cl.
*A61N 1/00* (2006.01)
*A61N 1/372* (2006.01)
(Continued)

(52) U.S. Cl.
CPC ......... *A61N 1/37288* (2013.01); *A61N 1/371* (2013.01); *A61N 1/3756* (2013.01);
(Continued)

(58) Field of Classification Search
CPC . A61N 1/37288; A61N 1/37217; A61N 1/371
See application file for complete search history.

(56) References Cited

U.S. PATENT DOCUMENTS 6,443,891 B1   9/2002  Grevious
6,704,602 B2   3/2004  Berg et al.
(Continued)

FOREIGN PATENT DOCUMENTS

CN      202933393 U     5/2013

*Primary Examiner* — Robert N Weiland
(74) *Attorney, Agent, or Firm* — Seager, Tufte & Wickhem LLP

(57) ABSTRACT

System and methods for energy adaptive communications between medical devices are disclosed. In one example, a medical device includes a communication module configured to deliver a plurality of pulses to tissue of a patient, where each pulse has an amount of energy. A control module operatively coupled to the communication module, may be configured to, for each delivered pulse, determine whether the delivered pulse produces an unwanted stimulation of the patient and to change the amount of energy of the plurality of pulses over time so as to identify an amount of energy that corresponds to an unwanted stimulation threshold for the pulses. The control module may then set a maximum energy value for communication pulses that is below the unwanted stimulation threshold, and may deliver communication pulses below the maximum energy value during communication with another medical device.

20 Claims, 16 Drawing Sheets

Related U.S. Application Data

(60) Provisional application No. 62/043,123, filed on Aug. 28, 2014.

(51) Int. Cl.
*A61N 1/375* (2006.01)
*A61N 1/37* (2006.01)
*A61N 1/39* (2006.01)

(52) U.S. Cl.
CPC ..... *A61N 1/37217* (2013.01); *A61N 1/37241* (2013.01); *A61N 1/37276* (2013.01); *A61N 1/3956* (2013.01)

(56) References Cited

U.S. PATENT DOCUMENTS

| | | |
|---|---|---|
| 7,738,964 B2 | 6/2010 | Von Arx et al. |
| 7,742,822 B2 | 6/2010 | Masoud et al. |
| 8,554,333 B2 | 10/2013 | Wu et al. |
| 8,571,678 B2 | 10/2013 | Wang |
| 8,744,572 B1 | 6/2014 | Greenhut et al. |
| 2008/0071318 A1 | 3/2008 | Brooke et al. |
| 2009/0210024 A1 | 8/2009 | Brooke |
| 2011/0245890 A1 | 10/2011 | Brisben et al. |
| 2012/0059436 A1 | 3/2012 | Fontaine et al. |
| 2012/0277606 A1 | 11/2012 | Ellingson et al. |
| 2013/0041422 A1 | 2/2013 | Jacobson |
| 2013/0060298 A1* | 3/2013 | Splett ............... A61N 1/371 607/28 |
| 2014/0214104 A1 | 7/2014 | Greenhut et al. |

* cited by examiner

ENERGY ADAPTIVE COMMUNICATION FOR MEDICAL DEVICES

CROSS-REFERENCE TO RELATED APPLICATIONS

This is a continuation of U.S. patent application Ser. No. 14/836,247, filed Aug. 26, 2015, which claims priority under 35 U.S.C. §119 to U.S. Provisional Application Ser. No. 62/043,123, filed Aug. 28, 2014, both of which are incorporated herein by reference.

TECHNICAL FIELD

The present disclosure generally relates to systems, devices, and methods for communicating information, and more particularly, to systems, devices, and methods for communicating information between medical devices in a power efficient manner.

BACKGROUND

Implantable medical devices are commonly used today to monitor a patient and/or deliver therapy to a patient. For example, implantable sensors are often used to monitor one or more physiological parameters of a patient, such as heart beats, heart sounds, ECG, respiration, etc. In another example, implantable neurostimulators can be used to provide neurostimulation therapy to a patient. In yet another example, pacing devices can be used to treat patients suffering from various heart conditions that may result in a reduced ability of the heart to deliver sufficient amounts of blood to a patient's body. Such heart conditions may lead to rapid, irregular, and/or inefficient heart contractions. To help alleviate some of these conditions, various devices (e.g., pacemakers, defibrillators, etc.) are often implanted in a patient's body. Such devices may monitor and provide electrical stimulation to the heart to help the heart operate in a more normal, efficient and/or safe manner. Regardless of the type of device, it is often desirable for the implantable medical device to communicate with another medical device.

SUMMARY

The present disclosure generally relates to systems, devices, and methods for communicating information, and more particularly, to systems, devices, and methods for communicating information between medical devices in an energy adaptive manner. In some instances, communication signals used for communication between medical devices may cause an unwanted effect in the patient. For example, the communication signals may be communication pulses that are sufficiently energetic to capture the heart, stimulate muscles and/or stimulate nerves. In some example, when this occurs, a maximum energy level test (MELT) may be conducted where the amount of energy of the communication pulses may be changed so as to identify an amount of energy that corresponds to an unwanted stimulation threshold. A maximum energy level for subsequent communication pulses may then be set below the unwanted stimulation threshold, and subsequent communication between medical devices may proceed. Reevaluating the unwanted stimulation threshold may occur from time to time and/or in response to a detected trigger event in order to provide an energy adaptive communication protocol over time. The present disclosure also describes techniques for adjusting the energy level of the communication pulses to reduce the amount of energy used during such communication while still achieving reliable communication.

In one example, a medical device comprises a communication module configured to deliver a plurality of pulses to tissue of a patient, where each pulse comprises an amount of energy; a control module operatively coupled to the communication module, the control module configured to: for each delivered pulse, determine whether the delivered pulse produces an unwanted stimulation of the patient; change the amount of energy of the plurality of pulses over time so as to identify an amount of energy that corresponds to an unwanted stimulation threshold for the communication pulses; set a maximum energy value for communication pulses that is below the unwanted stimulation threshold; and deliver communication pulses below the maximum energy value during communication with another device.

Alternatively or additionally, in any of the above examples, to set the maximum energy value for communication pulses that is below the unwanted stimulation threshold, the controller may be configured to set the maximum energy value a predetermined safety margin below the unwanted stimulation threshold.

Alternatively or additionally, in any of the above examples, the unwanted stimulation may be a capture of a heart of the patient.

Alternatively or additionally, any of the above examples may further comprise a pulse generator module for delivering pacing pulses to tissue of the patient, wherein to deliver a plurality of pulses to tissue of a patient, the communication module is configured to deliver a pulse in lieu of the pulse generator module delivering a pacing pulse, and the pulse generator module is further configured to deliver a safety pacing pulse if the pulse did not capture the heart.

Alternatively or additionally, in any of the above examples, the unwanted stimulation may be a stimulation of a nerve of the patient.

Alternatively or additionally, in any of the above examples, the unwanted stimulation may be a stimulation of a muscle of the patient.

Alternatively or additionally, in any of the above examples, the amount of energy of each pulse is defined at least in part by an amplitude, a pulse width, a morphology, or the specific vector via which the pulse is delivered.

Alternatively or additionally, in any of the above examples, to change the amount of energy of the plurality of pulses over time, the controller may be configured to change either the amplitude or the pulse width of each pulse.

Alternatively or additionally, in any of the above examples, to change the amount of energy of the plurality of pulses over time, the controller may be configured to change both the amplitude and the pulse width of each pulse.

Alternatively or additionally, in any of the above examples, the medical device may be further configured to deliver the plurality of pulses, change the amount of energy of the plurality of pulses, and set the maximum energy value for communication pulses that is below the unwanted stimulation threshold in a repeating manner.

Alternatively or additionally, in any of the above examples, the medical device may be further configured to deliver the plurality of pulses, change the amount of energy of the plurality of pulses, and set the maximum energy value for communication pulses that is below the unwanted stimulation threshold in response to a trigger event.

Alternatively or additionally, in any of the above examples, the medical device is a leadless cardiac pacemaker (LCP).

Alternatively or additionally, in any of the above examples, the another medical device is a subcutaneous implantable cardioverter-defibrillator (S-ICD).

Alternatively or additionally, in any of the above examples, the medical device is an S-ICD.

Alternatively or additionally, in any of the above examples, the another medical device is an LCP.

In another example, a method for setting an energy level for communication pulses of a medical device comprises delivering a plurality of pulses to tissue of a patient, where each pulse includes an amount of energy, and for each delivered pulse, determining whether the delivered pulse produces an unwanted stimulation of the patient; changing the amount of energy of the plurality of pulses over time so as to identify an amount of energy that corresponds to an unwanted stimulation threshold for the pulses; and setting a maximum energy value for communication pulses that is below the unwanted stimulation threshold.

Alternatively or additionally, in any of the above examples, the maximum energy value is set a predetermined safety margin below the unwanted stimulation threshold.

Alternatively or additionally, in any of the above examples, the unwanted stimulation is a capture of a heart of the patient.

Alternatively or additionally, in any of the above examples, delivering a plurality of pulses to tissue of a patient comprises delivering a pulse in lieu of a pacing pulse, and delivering a safety pacing pulse if the pulse did not capture the heart.

Alternatively or additionally, in any of the above examples, the unwanted stimulation is a stimulation of a nerve of the patient.

Alternatively or additionally, in any of the above examples, the unwanted stimulation is a stimulation of a muscle of the patient.

Alternatively or additionally, in any of the above examples, the amount of energy of each pulse is defined at least in part by an amplitude, a pulse width, a morphology, or the specific vector via which the pulse is delivered.

Alternatively or additionally, any of the above examples may further comprise repeating the delivering, changing and setting steps from time to time.

Alternatively or additionally, any of the above examples may further comprise repeating the delivering, changing and setting steps in response to a trigger event.

In yet another example, a medical device comprises: a communication module configured to deliver a plurality of pulses to tissue of a patient, where each pulse comprises an amount of energy; a control module operatively coupled to the communication module, the control module configured to: for each delivered pulse, determine whether the delivered pulse produces an unwanted stimulation of the patient; change the amount of energy of the plurality of pulses over time so as to identify an amount of energy that corresponds to an unwanted stimulation threshold for the pulses; set a maximum energy value for communication pulses that is below the unwanted stimulation threshold; and deliver communication pulses below the maximum energy value during communication with another device.

In still another example, a method for determining a minimum communication receive threshold for a medical device for use when receiving communication signals from another device comprises: setting the minimum communication receive threshold to a first level; determining a number of detected communication signals with the minimum communication receive threshold at the first level; changing the minimum communication receive threshold to a second level, wherein the second level is different than the first level; determining a number of detected communication signals with the minimum communication receive threshold at the second level; determining a value for the minimum communication receive threshold based on the determined numbers of detected communication signals; setting the minimum communication receive threshold to the determined value; and using the set minimum communication receive threshold during subsequent communication between the medical device and the another device.

Alternatively or additionally, in any of the above examples, at least some of the detected communication signals are noise signals interpreted by the medical device as communication signals when the minimum communication receive threshold is set at the second level.

Alternatively or additionally, in any of the above examples, determining the value for the minimum communication receive threshold based on the determined numbers of detected communication signals comprises determining the value based on a signal to noise ratio.

Alternatively or additionally, any of the above examples may further comprise determining the number of detected communication signals with the minimum communication receive threshold at the first level and determining the number of detected communication signals with the minimum communication receive threshold at the second level during periods of no intrinsic cardiac activity.

Alternatively or additionally, in any of the above examples, the second level is less than the first level.

Alternatively or additionally, in any of the above examples, the second level is greater than the first level.

In another example, a medical device comprises: a communication module configured to receive a plurality of communication signals from another device; a control module operatively coupled to the communication module, the control module configured to: set a minimum communication receive threshold to a first level; determine a number of detected communication signals with the minimum communication receive threshold at the first level; change the minimum communication receive threshold to a second level, wherein the second level is different than the first level; determine a number of detected communication signals with the minimum communication receive threshold at the second level; determine a value for the minimum communication receive threshold based on the determined number of detected communication signals; set the minimum communication receive threshold to the determined value; and use the set minimum communication receive threshold during subsequent communication between the medical device and the other device.

Alternatively or additionally, in any of the above examples, the maximum energy value is set a predetermined safety margin below the unwanted stimulation threshold.

In another example, a method for adjusting a communication protocol between a plurality of medical devices comprises: with a first medical device, delivering one or more first pulses where each first pulse includes a first amount of energy; determining a number of the one or more first pulses received by a second medical device; with the first medical device, delivering one or more second pulses where each second pulse includes a second amount of energy; determining a number of the one or more second pulses received by the second medical device; and adjusting a minimum communication pulse energy for the first medical device when communicating with the second medical device based on the number of the one or more first pulses received by the second medical device and the number of the one or more second pulses received by the second medical device.

Alternatively or additionally, in any of the above examples, the amount of energy of each pulse is defined at least in part by an amplitude, a pulse width, a morphology, or the specific vector via which the pulse is delivered.

Alternatively or additionally, in any of the above examples, adjusting the minimum communication pulse energy for the first medical device when communicating with the second medical device comprises adjusting the pulse width of each communication pulse used to communicate with the second medical device.

Alternatively or additionally, in any of the above examples, adjusting the minimum communication pulse energy for the first medical device when subsequently communicating with the second medical device comprises adjusting the amplitude of each communication pulse used to communicate with the second medical device.

Alternatively or additionally, in any of the above examples, adjusting the minimum communication pulse energy for the first medical device when subsequently communicating with the second medical device comprises adjusting the pulse width and the amplitude of each communication pulse used to communicate with the second medical device.

Alternatively or additionally, in any of the above examples, adjusting the minimum communication pulse energy for the first medical device when communicating with the second medical device based on the number of the one or more first pulses received by the second medical device and the number of the one or more second pulses received by the second medical device comprises setting the minimum communication pulse energy for the first medical device when communicating with the second medical device to the amount of energy of the one or more pulses with the lowest acceptable number of pulses received by the second medical device.

Alternatively or additionally, any of the above examples may further comprise adding a predetermined safety margin to the minimum communication pulse energy.

Alternatively or additionally, any of the above examples may further comprise determining whether the adjusted minimum communication pulse energy overlaps a maximum energy threshold.

Alternatively or additionally, any of the above examples, may further comprise, after determining the adjusted minimum communication pulse energy overlaps the maximum energy threshold, by the first medical device, entering a safe communication mode.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
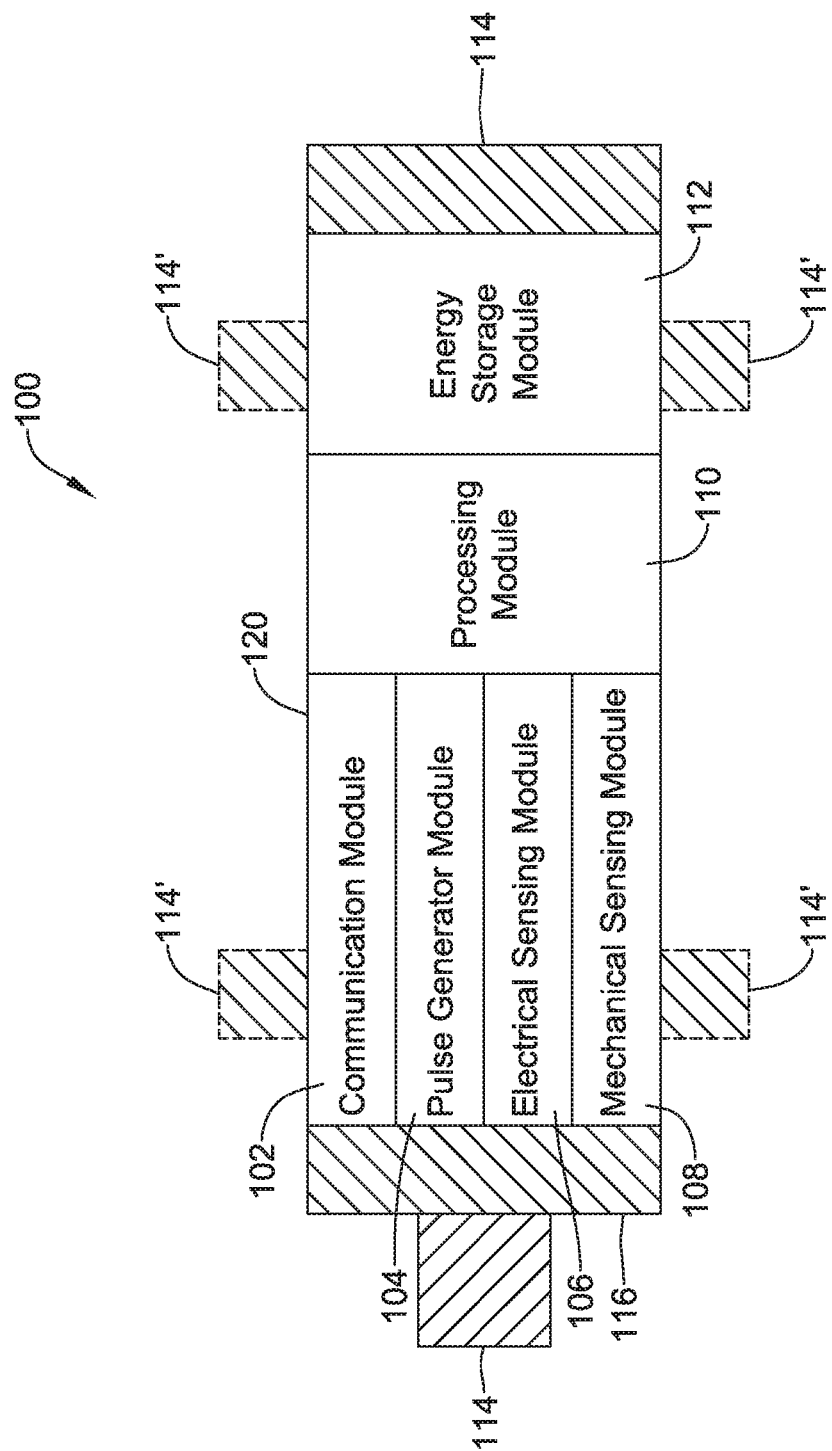
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

This disclosure describes systems, devices, and methods for communicating information, and more particularly, to systems, devices, and methods for communicating information between medical devices in an energy adaptive manner. In some instances, communication signals used for communication between medical devices may cause an unwanted effect in the patient. For example, the communication signals may be communication pulses that are sufficiently energetic to capture the heart, stimulate muscles and/or stimulate nerves. In some example, when this occurs, a maximum energy level test (MELT) may be conducted where the amount of energy of the communication pulses may be changed so as to identify an amount of energy that corresponds to an unwanted stimulation threshold. A maximum energy level for subsequent communication pulses may then be set below the unwanted stimulation threshold, and subsequent communication between medical devices may proceed. Reevaluating the unwanted stimulation threshold may occur from time to time and/or in response to a detected trigger event to provide energy adaptive communication over time. The present disclosure also describes techniques for adjusting the energy level of the communication pulses to reduce the amount of energy used during such communication while still achieving reliable communication.

FIG. 1 is a conceptual drawing of an exemplary leadless cardiac pacemaker (LCP) that may be implanted into a patient and may operate to sense physiological signals and parameters and deliver one or more types of electrical stimulation therapy to tissues of the patient. Example electrical stimulation therapy includes anti-tachycardia pacing (ATP) therapy, cardiac resynchronization therapy (CRT), bradycardia therapy, various types of pacing therapy including rate responsive pacing therapy, and/or the like. As can be seen in FIG. 1, LCP 100 may be a compact device with all components housed within LCP 100 or directly on housing 120. LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 but exposed to the tissue and/or blood surrounding LCP 100. Electrodes 114 may generally conduct electrical signals to and from LCP 100 and the surrounding tissue and/or blood. Such electrical signals can include communication pulses, electrical stimulation pulses, and intrinsic cardiac electrical signals. Intrinsic cardiac electrical signals may consist of the electrical signals generated by the heart and may be represented by an electrocardiogram (ECG). Electrodes 114 can be made up of one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In examples where electrodes 114 are secured directly to housing 120, electrodes 114 may have an insulative portion that electrically isolates electrodes 114 from adjacent electrodes, housing 120, and/or other portions of LCP 100. Some or all of electrodes 114 may be spaced from housing 120 and connected to housing 120 and/or other components of LCP 100 through connecting wires. In such embodiments, the electrodes 114 may be placed on a on a tail that extends from the housing 120. As shown in FIG. 1, in some examples, LCP 100 may additionally include electrodes 114'. Electrodes 114' are similar to electrodes 114 except that electrodes 114' are disposed on the sides of LCP 100 and increase the number of electrodes by which LCP 100 may deliver communication pulses and electrical stimulation pulses and/or sense for intrinsic cardiac electrical signals, communication pulses, and/or electrical stimulation pulses.

Electrodes 114 and/or 114' may have any of a variety of sizes and/or shapes, and may be spaced at any of a variety of distances. For example, electrodes 114 may have a diameter of two to twenty millimeters (mm). However, in other examples, electrodes 114 and/or 114' may have a diameter of two, three, five, seven millimeters (mm), or any other suitable diameter, dimension and shape. Example lengths for electrodes 114 and/or 114' include a length of zero, one, three, five, ten millimeters (mm), or any other suitable length. As used herein, the length is a dimension of electrodes 114 and/or 114' that extends away from housing 120. Additionally, at least some of electrodes 114 and/or 114' may be spaced from one another by a distance of twenty, thirty, forty, fifty millimeters (mm), or any other suitable distance. The electrodes 114 and/or 114' of a single device may have different sizes with respect to each other, and the spacing of the electrodes on the device may not be uniform.

Communication module 102 may be electrically coupled to electrodes 114 and/or 114' and configured to deliver communication pulses to tissues of the patient for communicating with other devices such as sensors, programmers, other medical devices, and the like. Communication pulses, as used herein, may be any modulated signal that conveys information to another device, either by itself or in conjunction with one or more other modulated signals. In some examples, communication pulses are limited to only including sub-threshold signals which convey information. Such other devices may be located either external or internal to the patient's body. Communication module 102 may additionally be configured to sense for communication pulses delivered by the other devices, which are located externally to LCP 100. Irrespective of the location, LCP and the other devices may communicate with each other via communication module 102 to accomplish one or more desired functions. Some example functions include storing communicated data, using communicated data for determining occurrences of arrhythmias, coordinating delivery of electrical stimulation therapy, and/or other functions.

LCP 100 and the other devices may use the delivered communication pulses to communicate raw information, processed information, messages, and/or other data. Raw information may include information such as sensed electrical signals (e.g. a sensed ECG), signals gathered from coupled sensors, and the like. In some examples, the raw information may include signals that have been filtered using one or more signal processing techniques. Processed information may include any information that has been determined by LCP 100. For example, processed information may include a determined heart rate, timings of determined heartbeats, timings of other determined events, determinations of threshold crossings, expirations of monitored time periods, and determined parameters such as activity parameters, blood-oxygen parameters, blood pressure parameters, heart sound parameters, and the like. Messages may include instructions directing another device to take action, notifications of imminent actions of the sending device, requests for reading from the receiving device or writing data to the receiving device.

In at least some examples, communication module 102 (or LCP 100) may further include switching circuitry to selectively connect one or more of electrodes 114 and/or 114' to communication module 102 in order to select via which electrodes 114 and/or 114' communication module 102 delivers the communication pulses. Additionally, communication module 102 may be configured to use one or more methods for communicating with other devices. For example, communication module 102 may communicate via conducted signals, radiofrequency (RF) signals, optical signals, acoustic signals, inductive coupling, and/or any other signals or methods suitable for communication.

Pulse generator module 104 of LCP 100 may also be electrically connected to one or more of electrodes 114 and/or 114'. Pulse generator module 104 may be configured to generate electrical stimulation pulses and deliver the electrical stimulation pulses to tissues of a patient via electrodes 114 and/or 114' electrodes in order to effectuate one or more electrical stimulation therapies. Electrical stimulation pulses as used herein are meant to encompass any electrical signals that may be delivered to tissue of a patient for purposes of treatment of any type of disease or abnormality. When used to treat heart diseases or abnormalities, the electrical stimulation pulses may generally be configured so as to capture the heart of the patient—cause the heart to contract in response to the delivered electrical stimulation pulse. In at least examples where pulse generator 104 is configured to generate specific types of electrical stimulation pulses termed defibrillation/cardioversion pulses, pulse generator module 104 may include one or more capacitor elements.

Pulse generator module 104 may include capability to modify the electrical stimulation pulses, such as by adjusting a pulse width or amplitude of the electrical stimulation pulses, in order to ensure that the delivered electrical stimulation pulses consistently capture the heart. Pulse generator module 104 may use energy stored in energy storage module 112 to generate the electrical stimulation pulses. In at least some examples, pulse generator module 104 (or LCP 100) may further include switching circuitry to selectively connect one or more of electrodes 114 and/or 114' to pulse generator module 104 in order to select via which electrodes 114 and/or 114' pulse generator 104 delivers the electrical stimulation pulses.

In some examples, LCP 100 may include electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114'. In some examples, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, blood pressure sensors, heart sound sensors, blood-oxygen sensors, and/or other sensors which measure one or more physiological parameters of the heart and/or patient. Mechanical sensing module 108 may gather signals from the sensors indicative of the various physiological parameters. Both electrical sensing module 106 and mechanical sensing module 108 may be further connected to processing module 110 and may provide signals representative of the sensed cardiac electrical signals and/or physiological signals to processing module 110. Although described with respect to FIG. 1 as separate sensing modules, in some examples, electrical sensing module 106 and mechanical sensing module 108 may be combined into a single module.

Processing module 110 may be configured to control the operation of LCP 100. For example, processing module 110 may be configured to receive cardiac electrical signals from electrical sensing module 106 and/or physiological signals from mechanical sensing module 108. Based on the received signals, processing module 110 may determine occurrences and types of arrhythmias. Processing module 110 may further receive information from communication module 102. In some examples, processing module 110 may additionally use such received information to determine occurrences and types of arrhythmias. However, in other examples, LCP 100 may use the received information instead of the signals received from electrical sensing module 106 and/or mechanical sensing module 108—for instance if the received information is more accurate than the signals received from electrical sensing module 106 and/or mechanical sensing module 108 or if electrical sensing module 106 and/or mechanical sensing module 108 have been disabled or omitted from LCP 100.

Based on any determined arrhythmias, processing module 110 may then control pulse generator module 104 to generate electrical stimulation pulses in accordance with one or more electrical stimulation therapies to treat the determined arrhythmias. For example, processing module 110 may control pulse generator module 104 to generate pacing pulses with varying parameters and in different sequences to effectuate one or more electrical stimulation therapies. In controlling pulse generator module 104 to deliver bradycardia pacing therapy, processing module 110 may control pulse generator module 104 to deliver pacing pulses designed to capture the heart of the patient at a regular interval to prevent the heart of a patient from falling below a predetermined threshold. For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Processing module 110 may then control pulse generator module 104 to reduce the rate of delivered pacing pulses down to a safe level. In CRT, processing module 110 may control pulse generator module 104 to deliver pacing pulses in coordination with another device to cause the heart to contract more efficiently. Additionally, in cases where pulse generator module 104 is capable of generating defibrillation and/or cardioversion pulses for defibrillation/cardioversion therapy, processing module 110 may control pulse generator module 104 to generate such defibrillation and/or cardioversion pulses. In other examples, processing module 110 may control pulse generator module 104 to generate electrical stimulation pulses to provide electrical stimulation therapies different than those described herein to treat one or more detected cardiac arrhythmias.

Aside from controlling pulse generator module 104 to generate different types of electrical stimulation pulses and in different sequences, in some examples, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may ensure that LCP 100 is able to provide effective delivery of electrical stimulation therapy.

In some examples, processing module 110 may further control communication module 102 to send information to other devices. For example, processing module 110 may control communication module 102 to generate one or more communication pulses for communicating with other devices of a system of devices. For instance, processing module 110 may control communication module 102 to generate communication pulses in particular sequences, where the specific sequences convey different data to other devices. Communication module 102 may also conduct any received communication signals to processing module 110 for potential action by processing module 110.

In further examples, processing module 110 may additionally control switching circuitry by which communication module 102 and pulse generator module 104 deliver communication pulses and electrical stimulation pulses to tissue of the patient. As described above, both communication module 102 and pulse generator module 104 may include circuitry for connecting one or more electrodes 114 and/114' to communication module 102 and pulse generator module 104 so those modules may deliver the communication pulses and electrical stimulation pulses to tissue of the patient. The specific combination of one or more electrodes by which communication module 102 and pulse generator module 104 deliver communication pulses and electrical stimulation pulses influence the reception of communication pulses and/or the effectiveness of electrical stimulation pulses. Although it was described that each of communication module 102 and pulse generator module 104 may include switching circuitry, in some examples LCP 100 may have a single switching module connected to all of communication module 102, pulse generator module 104, and electrodes 114 and/or 114'. In such examples, processing module 110 may control the single switching module to connect modules 102/104 and electrodes 114/114'.

In some examples, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby increasing the battery life of LCP 100. In other examples, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip.

Processing module 110, in additional examples, may further include a memory circuit and processing module 110 may store information on and read information from the memory circuit. In other examples, LCP 100 may include a separate memory circuit (not shown) that is in communication with processing module 110, such that processing module 110 may read and write information to and from the separate memory circuit. The memory circuit, whether part of processing module 110 or separate from processing module 110 may have address lengths of, for example, eight bits. However, in other examples, the memory circuit may have address lengths of sixteen, thirty-two, or sixty-four bits, or any other bit length that is suitable. Additionally, the memory circuit may be volatile memory, non-volatile memory, or a combination of both volatile memory and non-volatile memory.

Energy storage module 112 may provide a power source to LCP 100 for its operations. In some examples, energy storage module 112 may be a non-rechargeable lithium-based battery. In other examples, the non-rechargeable battery may be made from other suitable materials known in the art. Because LCP 100 is an implantable device, access to LCP 100 may be limited. In such circumstances, it is necessary to have sufficient energy capacity to deliver therapy over an extended period of treatment such as days, weeks, months, or years. In some examples, energy storage module 112 may a rechargeable battery in order to facilitate increasing the useable lifespan of LCP 100. In still other examples, energy storage module 112 may be other types of energy storage devices such as capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix anchor 116 within the cardiac tissue. In other examples, anchor 116 may include other structures such as barbs, spikes, or the like to facilitate engagement with the surrounding cardiac tissue.

Figure 2:
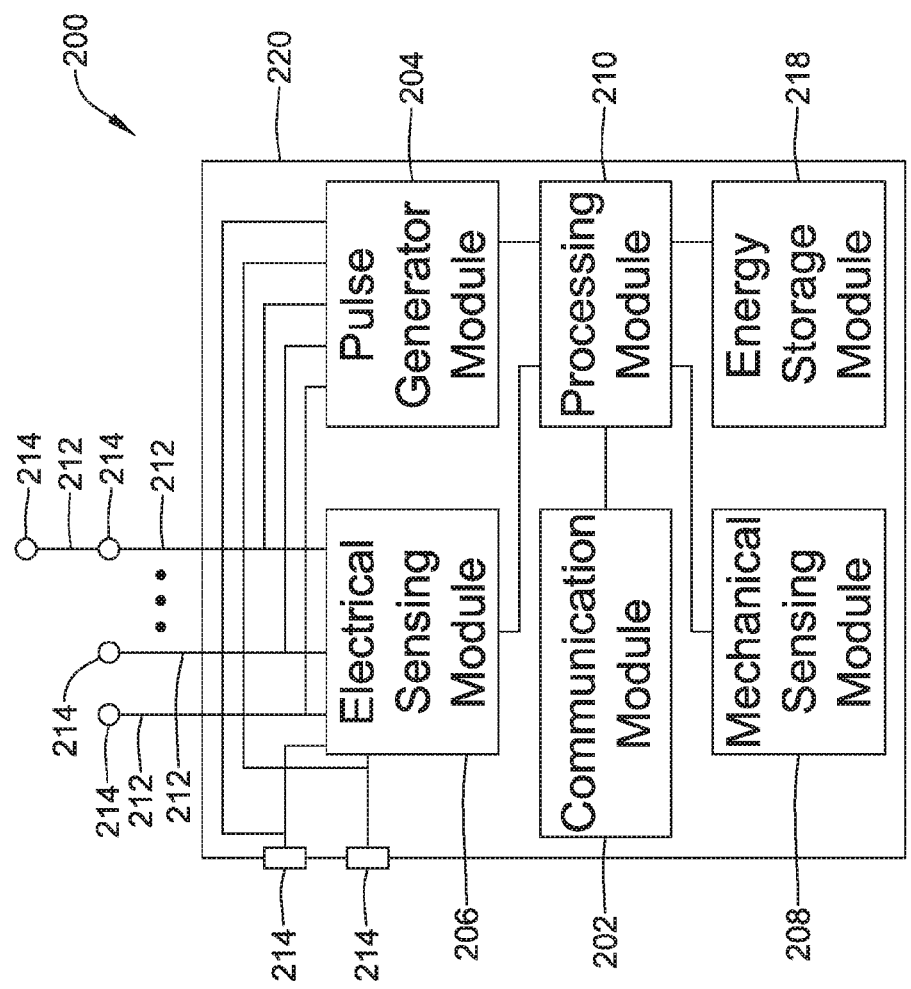
FIG. 2 is a schematic block diagram of another illustrative medical device that may be used in conjunction with the LCP of FIG. 1.

FIG. 2 depicts an example of another device, medical device (MD) 200, which may operate to sense physiological signals and parameters and deliver one or more types of electrical stimulation therapy to tissues of the patient. In the example shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. However, in some examples, MD 200 may have a larger volume within housing 220. In such examples, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some examples, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead 212. For example, one or more electrodes 214 may be connected directly to housing 220.

Leads 212, in some examples, may additionally contain one or more sensors, such as accelerometers, blood pressure sensors, heart sound sensors, blood-oxygen sensors, and/or other sensors which are configured to measure one or more physiological parameters of the heart and/or patient. In such examples, mechanical sensing module 208 may be in electrical communication with leads 212 and may receive signals generated from such sensors.

While not required, in some examples MD 200 may be an implantable medical device. In such examples, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such examples, leads 212 may be implanted at one or more various locations within the patient, such as within the heart of the patient, adjacent to the heart of the patient, adjacent to the spine of the patient, or any other desired location.

In some examples, MD 200 may be an implantable cardiac pacemaker (ICP). In these examples, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some examples, MD 200 may additionally be configured to provide defibrillation/cardioversion therapy.

In some instances, MD 200 may be an implantable cardioverter-defibrillator (ICD). In such examples, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia. In other examples, MD 200 may be a subcutaneous implantable cardioverter-defibrillator (S-ICD). In examples where MD 200 is an S-ICD, one of leads 212 may be a subcutaneously implanted lead. In at least some examples where MD 200 is an S-ICD, MD 200 may include only a single lead which is implanted subcutaneously but outside of the chest cavity, however this is not required.

In some examples, MD 200 may not be an implantable medical device. Rather, MD 200 may be a device external to the patient's body, and electrodes 214 may be skin-electrodes that are placed on a patient's body. In such examples, MD 200 may be able to sense surface electrical signals (e.g. electrical cardiac signals that are generated by the heart or electrical signals generated by a device implanted within a patient's body and conducted through the body to the skin). In such examples, MD 200 may be configured to deliver various types of electrical stimulation therapy, including, for example, defibrillation therapy.

Figure 3:
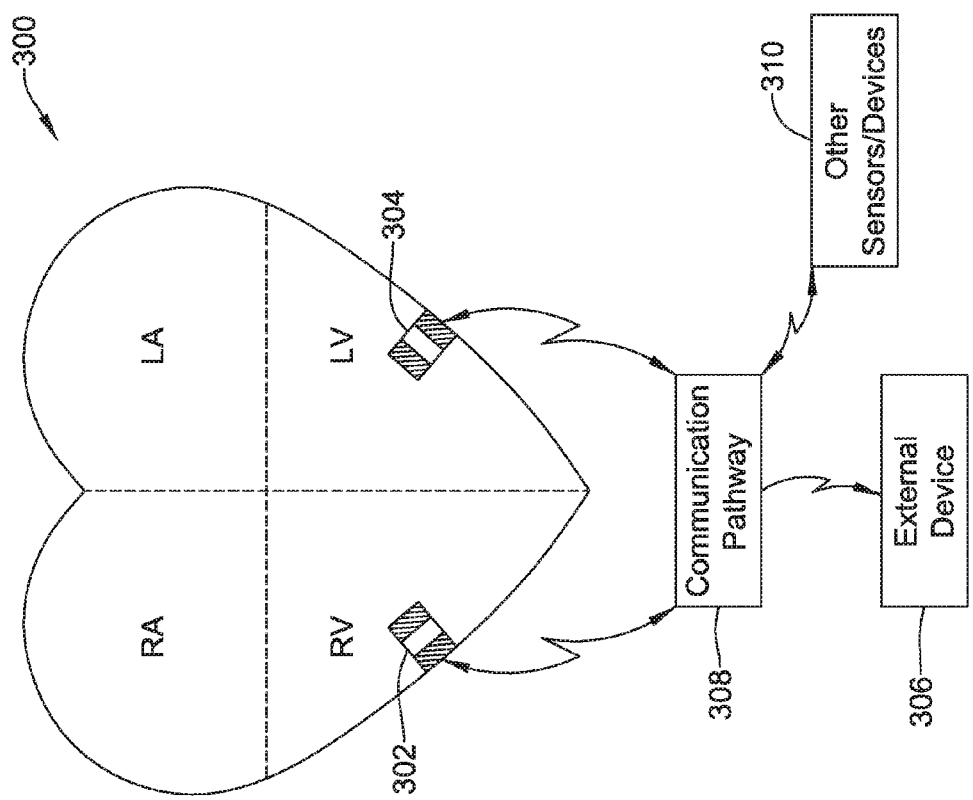
FIG. 3 is a schematic diagram of an exemplary medical system that includes multiple LCPs and/or other devices in communication with one another.

FIG. 3 illustrates an example of a medical device system and a communication pathway through which multiple medical devices 302, 304, 306, and/or 310 of the medical device system may communicate. In the example shown, medical device system 300 may include LCPs 302 and 304, external medical device 306, and other sensors/devices 310. External device 306 may be a device disposed external to a patient's body, as described previously with respect to MD 200. Other sensors/devices 310 may be any of the devices described previously with respect to MD 200, such as ICPs, ICDs, and S-ICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one example, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some examples, the various devices of system 300 may communicate via pathway 308 using multiple signal types. For instance, other sensors/device 310 may communicate with external device 306 using a first signal type (e.g. RF communication) but communicate with LCPs 302/304 using a second signal type (e.g. conducted communication). Further, in some examples, communication between devices may be limited. For instance, as described above, in some examples, LCPs 302/304 may communicate with external device 306 only through other sensors/devices 310, where LCPs 302/304 send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses have an amplitude/pulse width designed to not capture the heart. Although, in some cases, the amplitude/pulse width of the delivered electrical communication pulses may be above the capture threshold of the heart, but may be delivered during a refractory period of the heart and/or may be incorporated in or modulated onto a pacing pulse, if desired.

Delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 4:
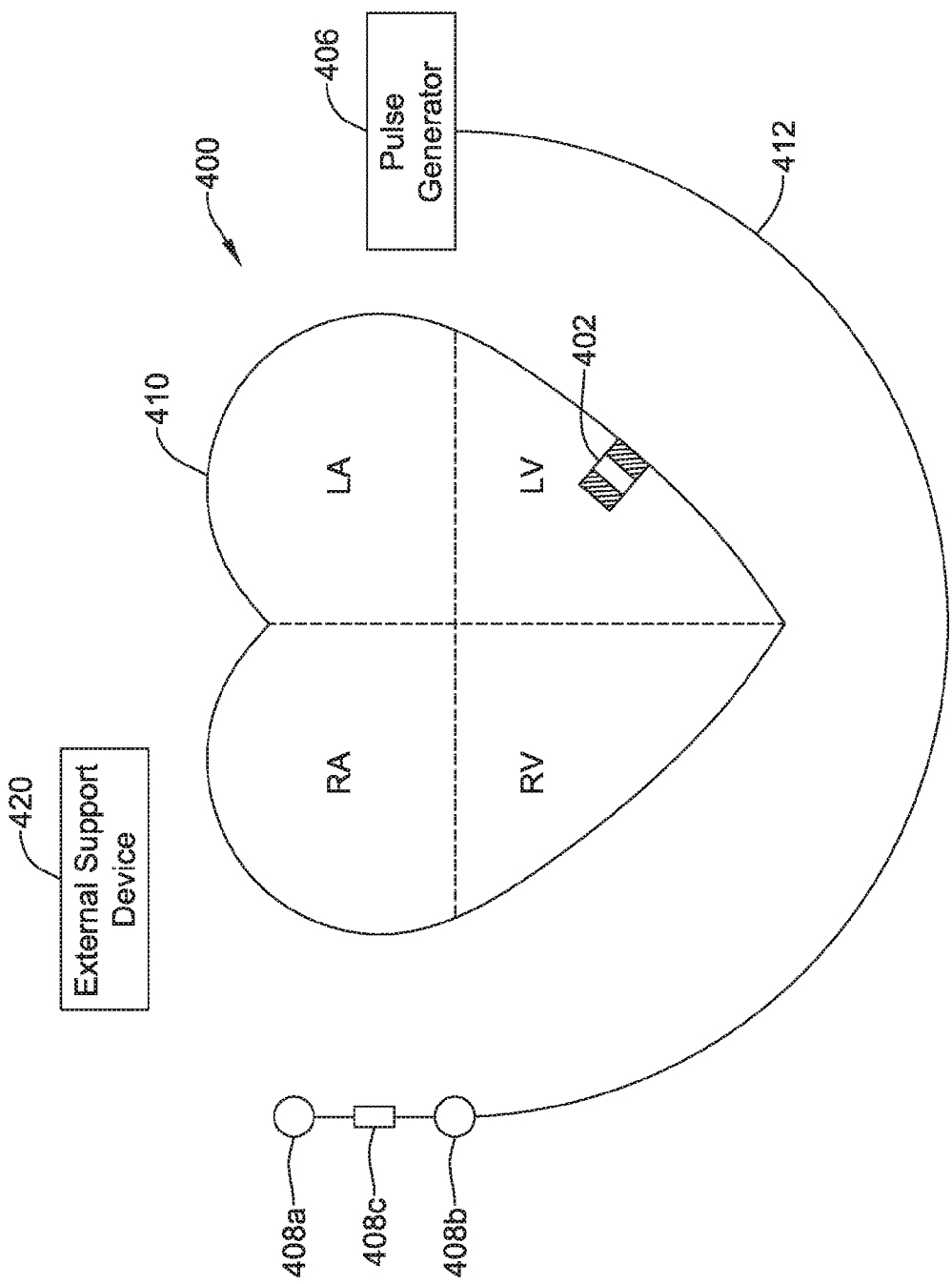
FIG. 4 is a schematic diagram of a system including an LCP and another medical device, in accordance with yet another example of the present disclosure.
Figure 5:
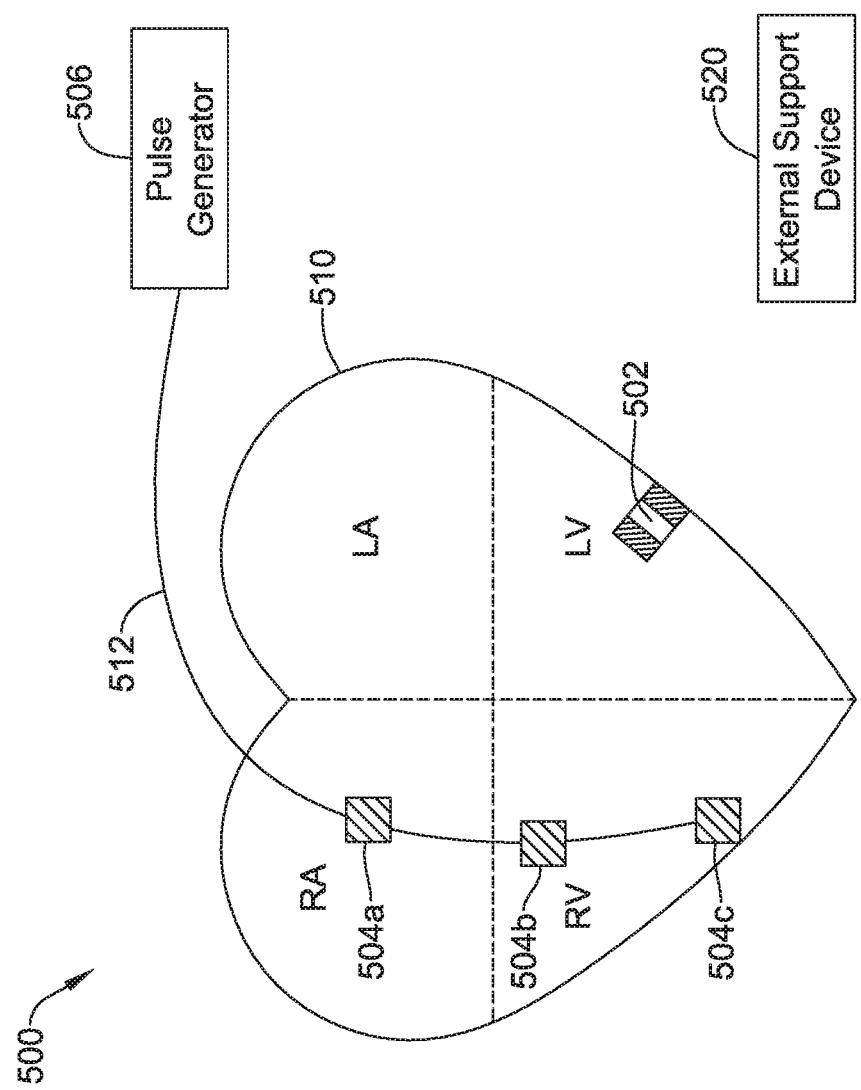
FIG. 5 is a schematic diagram of a system including an LCP and another medical device, in accordance with another example of the present disclosure.

FIGS. 4 and 5 show illustrative medical device systems that may be configured to operate according to techniques disclosed herein. For example, the systems may include multiple devices that are implanted within a patient and are configured to sense physiological signals, determine occurrences of cardiac arrhythmias, and deliver electrical stimulation to treat detected cardiac arrhythmias. In FIG. 4, an LCP 402 is shown fixed to the interior of the left ventricle of the heart 410, and a pulse generator 406 is shown coupled to a lead 412 having one or more electrodes 408*a*-408*c*. In some cases, the pulse generator 406 may be part of a subcutaneous implantable cardioverter-defibrillator (S-ICD), and the one or more electrodes 408*a*-408*c* may be positioned subcutaneously adjacent the heart. LCP 402 may communicate with the S-ICD, such as via communication pathway 308. The locations of LCP 402, pulse generator 406, lead 412, and electrodes 408*a*-*c* depicted in FIG. 4 are just exemplary. In other examples of system 400, LCP 402 may be positioned in the right ventricle, right atrium, or left atrium of the heart, as desired. In still other examples, LCP 402 may be implanted externally adjacent to heart 410 or even remote from heart 410.

In FIG. 5, an LCP 502 is shown fixed to the interior of the left ventricle of the heart 510, and a pulse generator 506 is shown coupled to a lead 512 having one or more electrodes 504*a*-504*c*. In some cases, the pulse generator 506 may be part of an implantable cardiac pacemaker (ICP) and/or an implantable cardioverter-defibrillator (ICD), and the one or more electrodes 504*a*-504*c* may be positioned in the heart 510. In some cases, LCP 502 may communicate with the implantable cardiac pacemaker (ICP) and/or an implantable cardioverter-defibrillator (ICD), such as via communication pathway 308. As with FIG. 4, the locations of LCP 502, pulse generator 506, lead 512, and electrodes 504*a*-*c* depicted in FIG. 5 are just exemplary. In other examples of system 500, LCP 502 may be positioned in the right ventricle, right atrium, or left atrium of the heart, as desired. In still other examples, LCP 502 may be implanted externally adjacent to heart 510 or even remote from heart 510. Additionally, in some examples lead 512 and/or electrodes 504*a*-*c* may be disposed in different chambers of heart 510, or pulse generator may include additional leads and/or electrodes that are disposed within or adjacent to heart 510.

The medical device systems 400 and 500 may also include an external support device, such as external support devices 420 and 520. External support devices 420 and 520 can be used to perform functions such as device identification, device programming and/or transfer of real-time and/or stored data between devices using one or more of the communication techniques described herein. As one example, communication between external support device 420 and the pulse generator 406 is performed via a wireless mode, and communication between the pulse generator 406 and LCP 402 is performed via a conducted mode. In some examples, communication between the LCP 402 and external support device 420 is accomplished by sending communication information through the pulse generator 406. However, in other examples, communication between the LCP 402 and external support device 420 may be via a communication module.

FIGS. 4-5 only illustrate a few examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406 or 506, with at least one LCP capable of delivering defibrillation therapy. Still another example may include one or more LCPs implanted along with a transvenous pacemaker and with or without an implanted SICD. In yet other examples, the configuration or placement of the medical devices, leads, and/or electrodes may be different from those depicted in FIGS. 4 and 5. Accordingly, it should be recognized that numerous other medical device systems, different from those depicted in FIGS. 4 and 5, may be operated in accordance with techniques disclosed herein. As such, the examples systems shown in FIGS. 4 and 5 should not be viewed as limiting in any way.

Even further, the disclosed techniques may be applied to devices that are not configured to detect and treat cardiac arrhythmias. For example, the techniques disclosed herein may be applicable to any medical devices or sensors which communicate with other devices and/or sensors. Accordingly, although the below examples are described with respect to an LCP device and an S-ICD device, this disclosure should not be construed to be so limiting. Additionally, the term 'communication pulses' as used below may correspond to pulses of any of the communication modalities mentioned previously, such as RF pulses, acoustic pulses, optical pulses, inductive pulses, and/or conducted pulses.

Using the system of FIG. 4 as one exemplary embodiment, LCP 402 and an S-ICD device (which can include pulse generator 406) may communicate with each other to, for example, detect cardiac abnormalities and to treat the detected cardiac abnormalities. As discussed above, LCP 402 and the S-ICD may communicate by sending communication pulses back and forth. The communication modules of both devices may be constantly listening for communication pulses and conveying any received communication pulses to processing units for further action. Because the communication modules are constantly listening, the communication modules may also receive signals other than communication pulses, for example noise signals. While in this example bi-directional communication is used, it is contemplated that in some systems only uni-directional communication may be used.

One issue that a device may encounter is interpreting noise signals as communication pulses. To combat interpreting noise signals as communication pulses, a device may employ a minimum communication receive threshold (MCRT). A MCRT may be a minimum energy threshold, and a device may only interpret received signals with energy levels above the MCRT as communication pulses. Of course, a device may employ other mechanisms for determining whether received signals are communication pulses (rather than noise signals or other signals), such as by analyzing the morphology or other features of the received signals. Another example mechanism for distinguishing between communication pulses and noise or other signals may be to use a pulse position parameter. For example, the device delivering the communication pulses may be configured to deliver the pulses at predetermined times or intervals of time. In such examples, if the receiving device received a signal that might appear to be a communication pulse but occurred outside of the predetermined times or intervals of time, the receiving device would interpret the received signal as other than a communication pulse. Such other mechanisms may be employed in place of an MCRT or in addition to an MCRT.

When a device determines that a received signals is a communication pulse, for example because the received signal has an energy level above the device's MCRT, and in some examples the received signal passes one or more other tests for whether the received signal is a communication pulse, the device may forward the received signal to one or more modules of the device for additional processing.

If the MCRT is set too low, noise may exceed the MCRT and may be improperly interpreted as a communication pulse. This can reduce the reliability and accuracy of the communicated data. When the MCRT is set too high, namely above what is required to reliably receive communication pulses, the sending medical device may expend extra energy sending each communication pulse. Since many medical devices have a limited power supply (e.g. a battery or other energy storage module), reducing the energy expended by each communication pulse can be an important consideration, and in some cases may substantially increase the useful life of the medical device.

Accordingly, to ensure that the MCRT is set to an appropriate level, a device, for example, LCP 402 and/or the S-ICD, may periodically perform an MCRT test. Typical periods between performing an MCRT test include once a day, once a week, once a month, or any other suitable period of time. In other examples, a device may perform an MCRT test based on trigger events, for example upon detection of a threshold amount of ignored communication attempts, temperature changes, voltage changes, or delivery of one or more therapies. For instance, a first device may send communication pulses to a second device that would normally cause the second device to response with one or more communication pulses. The first device may count a number of times that the first device has issued a communication without receiving a response from the second device. After the count reaches a threshold amount, the first device may trigger the second device to perform an MCRT test. In such examples, the first device may communicate the trigger to the second device using an alternative communication method, or the first device may adjust one or more parameters of the communication pulses before communicating the trigger to the second device, such as increasing the energy level of the communication pulses to a high level. In addition to the foregoing, and in some cases, a trigger event may include other events such as a change in a device parameter (e.g. pacing rate), a change in a patients activity (change in hemodynamic demand), a change in a patients posture, a detected patient event (e.g. defibrillation shock), a change in a communication parameter (e.g. frequency). A device may perform an MCRT test at implant, periodically and/or upon trigger events.

Figure 6:
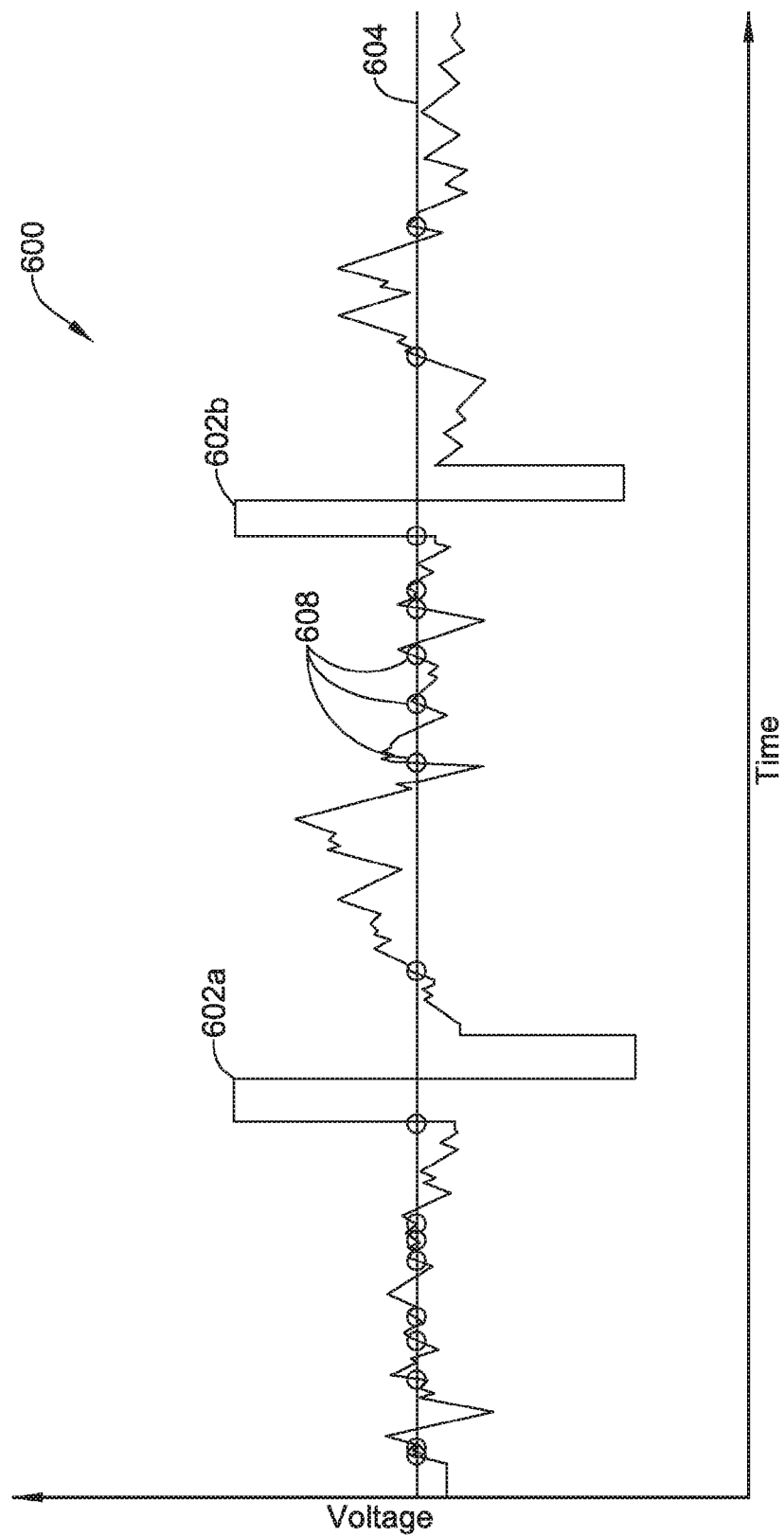
FIG. 6 is a graphical representation of an example sensed signal including communication pulses and noise signals, in accordance with an example of the present disclosure.
Figure 7:
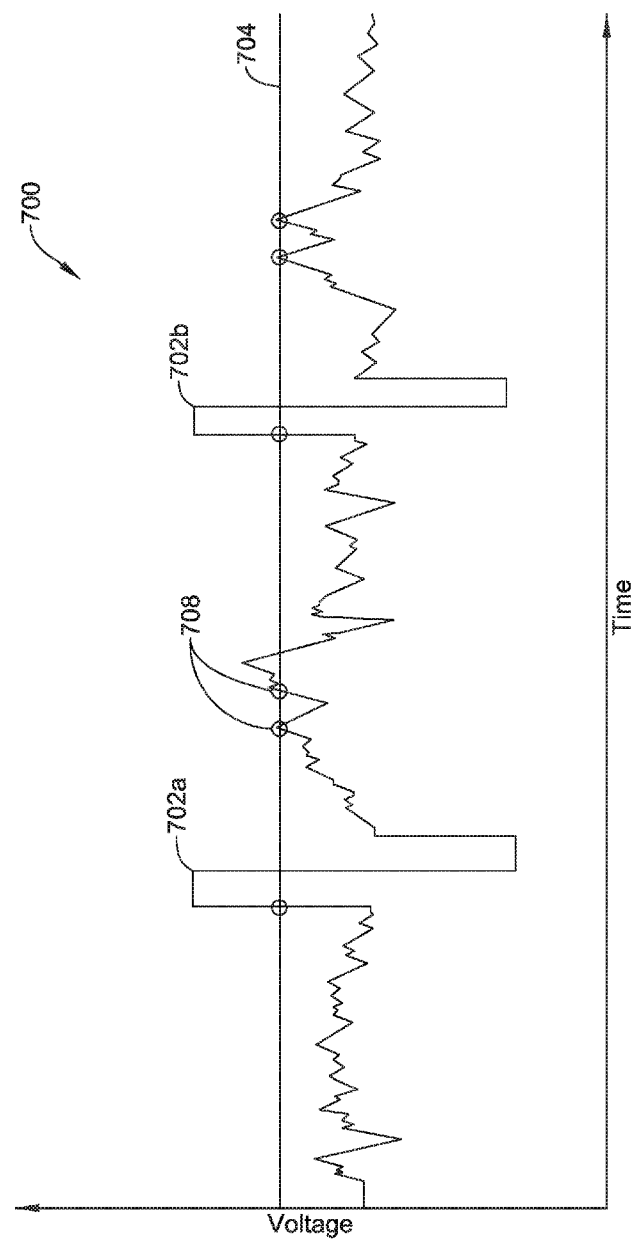
FIG. 7 is a graphical representation of an example sensed signal including communication pulses and noise signals, in accordance with an example of the present disclosure.
Figure 8:
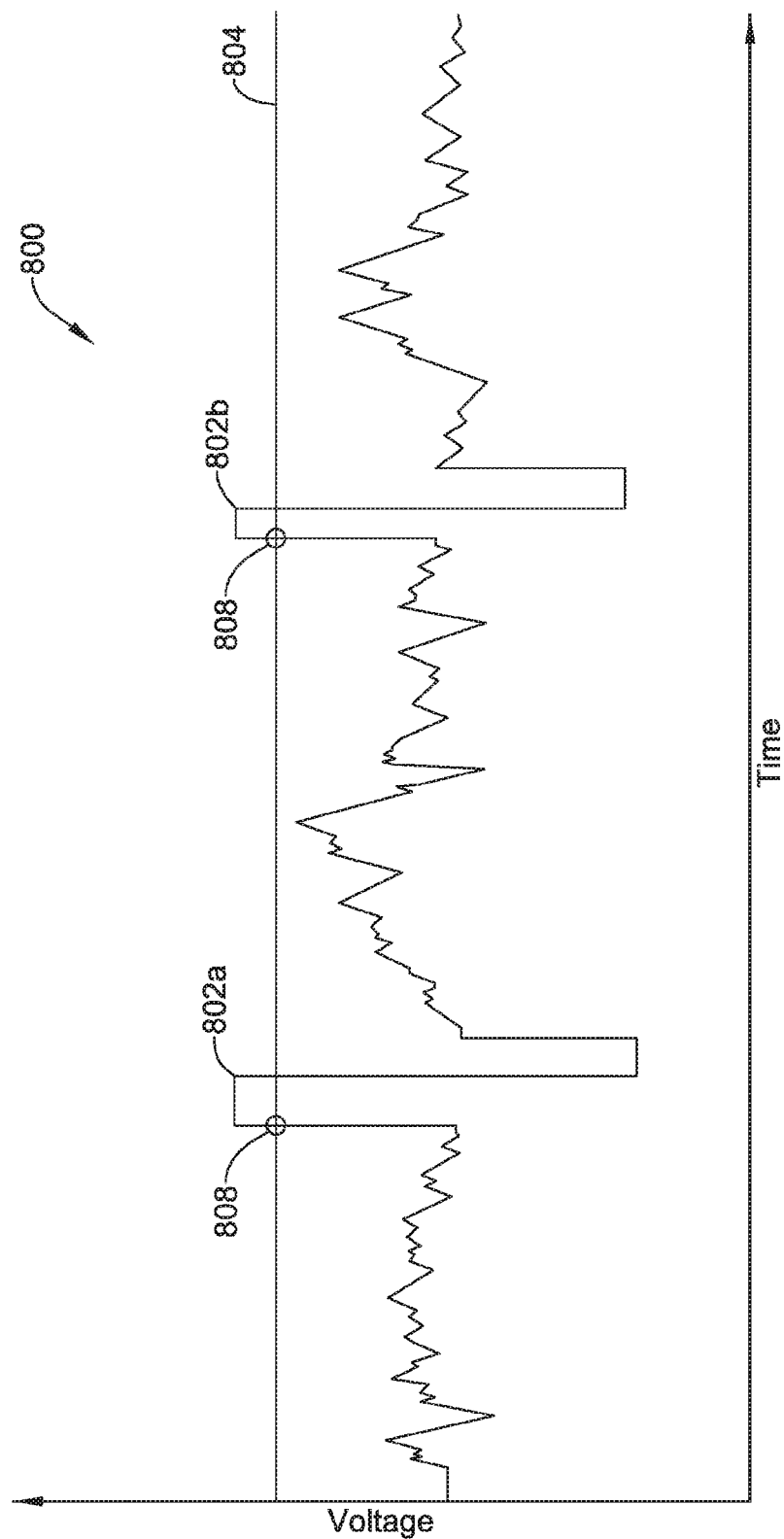
FIG. 8 is a graphical representation of an example sensed signal including communication pulses and noise signals, in accordance with an example of the present disclosure.

FIGS. 6-8 depict an example of received signals by a device, such as LCP 402, during MCRT tests. In some examples, LCP 402 may use the voltage of the received signals as a measure of an energy level of the received signals. In such examples, LCP 402 may set a voltage threshold as the MCRT, represented by voltage threshold 604. However, in other examples, LCP 402 may use other measures of energy to set a threshold as the MCRT during MCRT tests, for the example electrical power of the signal or the electrical energy of the signal. FIG. 6 depicts signal 600, which is an example signal received by LCP 402 during an MCRT test. During the MCRT test, LCP 402 may coordinate with the S-ICD for the S-ICD to deliver pulses to tissue of a patient during a predetermined period of time. In some examples, the pulses may be communication pulses. In other examples, the pulses may be test pulses. The test pulses may have similar parameters as communication pulses (e.g. pulse widths and amplitudes). However, the test pulses may not be configured to convey information to the receiving device, or the S-ICD may not deliver the test pulses in combinations which would convey information. The pulses may be different than stimulation and/or defibrillation pulses that the S-ICD may be configured to deliver during delivery of electrical stimulation therapy. Signal 600 may be received by LCP 402 during that predetermined period of time. The predetermined period of time may be a portion of the cardiac cycle between heartbeats—e.g. after a T-wave but before a subsequent P-wave. In other examples, the predetermined period of time may span multiple cardiac cycles. For instance, the predetermined period of time may include multiple non-consecutive periods of time, wherein each period of time is the portion of the cardiac cycle between heartbeats.

In any case, the S-ICD may be configured to deliver one or more pulses, such as pulses 602*a-b*, during the predetermined time period. The S-ICD may be configured in many different ways to deliver the pulses. For example, the S-ICD may be configured to deliver a set amount of pulses at regular intervals or at random intervals during the predetermined time period. Alternatively, the S-ICD may be configured to deliver a random or bounded-random number of pulses either at regular or irregular intervals during the predetermined time period. In some cases, the protocol by which the S-ICD delivers pulses during the MCRT test is also known to LCP 402. Accordingly, LCP 402 may know the timing and/or number of pulses that the S-ICD delivers during the MCRT test. Alternatively, the S-ICD may send a separate communication after the MCRT test to LCP 402 indicating the number of pulses the S-ICD delivered during the MCRT test.

During the MCRT test, LCP 402 may be receiving signals including pulses delivered by the S-ICD and various noise signals or other signals. In signal 600, pulses are represented by pulses 602*a-b* and noise or other signals are represented by the jagged portions before, between, and after pulses 602*a-b*. As depicted by markers 608, LCP 402 may count the number of times signal 600 crosses from below voltage threshold 604 to above voltage threshold 604. Once the predetermined time period has ended, LCP 402 may compare the number of detected crossings of voltage threshold 604 with the number of pulses delivered by the S-ICD. If the two numbers are acceptable, LCP 402 may then use voltage threshold 604 as the MCRT for future communications. In some examples, the numbers may be acceptable if the numbers match—e.g. the number of crossings of voltage threshold 604 equal the number of delivered pulses. However, in other examples, the numbers may be acceptable if the number of delivered pulses and the number of detected crossings of voltage threshold 604 are within a certain percentage of each other, such as five percent, ten percent, fifteen percent, twenty percent, or any other suitable percent or amount.

If the number of delivered pulses is lower than the number of detected crossings of voltage threshold 604, LCP 402 may set a new, higher voltage threshold and run the MCRT test again. LCP 402 may raise the voltage threshold for the next MCRT test by two millivolts, five millivolts, seven millivolts, ten millivolts, fifteen millivolts, twenty millivolts, or any other suitable value. In other examples, LCP 402 may raise the voltage threshold by a predetermined percentage of the current voltage threshold, such as three percent, five percent, seven percent, ten percent, fifteen percent, twenty percent, or any other suitable value. FIGS. 7 and 8 both depict MCRT tests including pulses 702a-b and 802a-b, and with LCP 402 using successively higher voltage thresholds 704 and 804, respectively. As can be seen, the detected crossings of the voltage thresholds, as represented by markers 708 and 808, become fewer with each successive increase of the voltage threshold. In the example of FIG. 8, the number of delivered pulses equals the number of detected crossings from below voltage threshold 804 to above voltage threshold 804. Accordingly, LCP 402 may set the MCRT equal to voltage threshold 804. In some cases, the MCRT may be set above the voltage threshold 804 by a margin amount.

If the number of delivered pulses is higher than the number of detected crossings of a voltage threshold during an MCRT test, LCP 402 may then set a new, lower voltage threshold and perform another MCRT test. In such situations, LCP 402 may have set the voltage threshold too high such that one or more of the delivered pulses did not reach the MCRT voltage threshold. In some cases, the sending device (e.g. SICD in this example), may provide pulses that are high during the MCRT test to help alleviate the number of times that the number of delivered pulses is higher than the number of detected crossings of the voltage threshold during an MCRT.

In some examples, LCP 402 may employ an MCRT test where, even after LCP 402 determines that the number of delivered pulses and the number of detected crossings of a voltage threshold during an MCRT test are acceptable, LCP 402 may still perform subsequent MCRT tests. For instance, in such examples, it may be possible for LCP 402 to set a lower MCRT and still ignore a large portion of noise signals or other signals. Reducing the MCRT in such a manner may thereby reduce the amount of energy used during communication. Accordingly, after determining that the number of delivered pulses and the number of detected crossings of a voltage threshold during an MCRT test are acceptable, LCP 402 may perform other MCRT test with a new, lower voltage threshold. Additional MCRT tests with stepped down voltage thresholds may be repeated until the number of delivered pulses and the number of detected crossings of a voltage threshold during an MCRT test are no longer comparatively acceptable.

In such examples, LCP 402 may lower the voltage threshold during a subsequent MCRT by a smaller amount than a last increase of the voltage threshold. For instance, LCP 402 may lower the voltage threshold by one-quarter, one-third, one-half, two-thirds, three-quarters, or any other suitable fraction of the last voltage threshold increase. Using FIGS. 7 and 8 as an example, if the voltage increase between voltage threshold 704 and voltage threshold 804 was ten millivolts, LCP 402 may set a new voltage threshold that is two and a half millivolts less voltage threshold 804 (e.g. one-quarter of the increase of the voltage threshold between voltage threshold 704 and voltage threshold 804) during a subsequent MCRT test. LCP 402 may perform multiple additional MCRT tests with new voltage thresholds lower than voltage threshold 804 by varying fractions of ten millivolts (e.g. five millivolts, six and two thirds millivolts, seven and a half millivolts, etc.) until the number of delivered pulses and detected crossings of the voltage threshold during the MCRT test become unacceptable (e.g. the numbers no longer match or fall within a predetermined percentage of each other). At this point, LCP 402 may then set the MCRT equal to the last voltage threshold for which the numbers were acceptable (sometimes plus a margin amount). In the example of FIGS. 7 and 8, if the number of delivered pulses and detected crossings of the voltage threshold were acceptable for the MCRT test using a voltage threshold two and a half millivolts less than voltage threshold 804 but were unacceptable for an MCRT test using a voltage threshold five millivolts less than voltage threshold 804, LCP 402 may set the MCRT equal to the voltage threshold that is two and a half millivolts less than voltage threshold 804.

Figure 9:
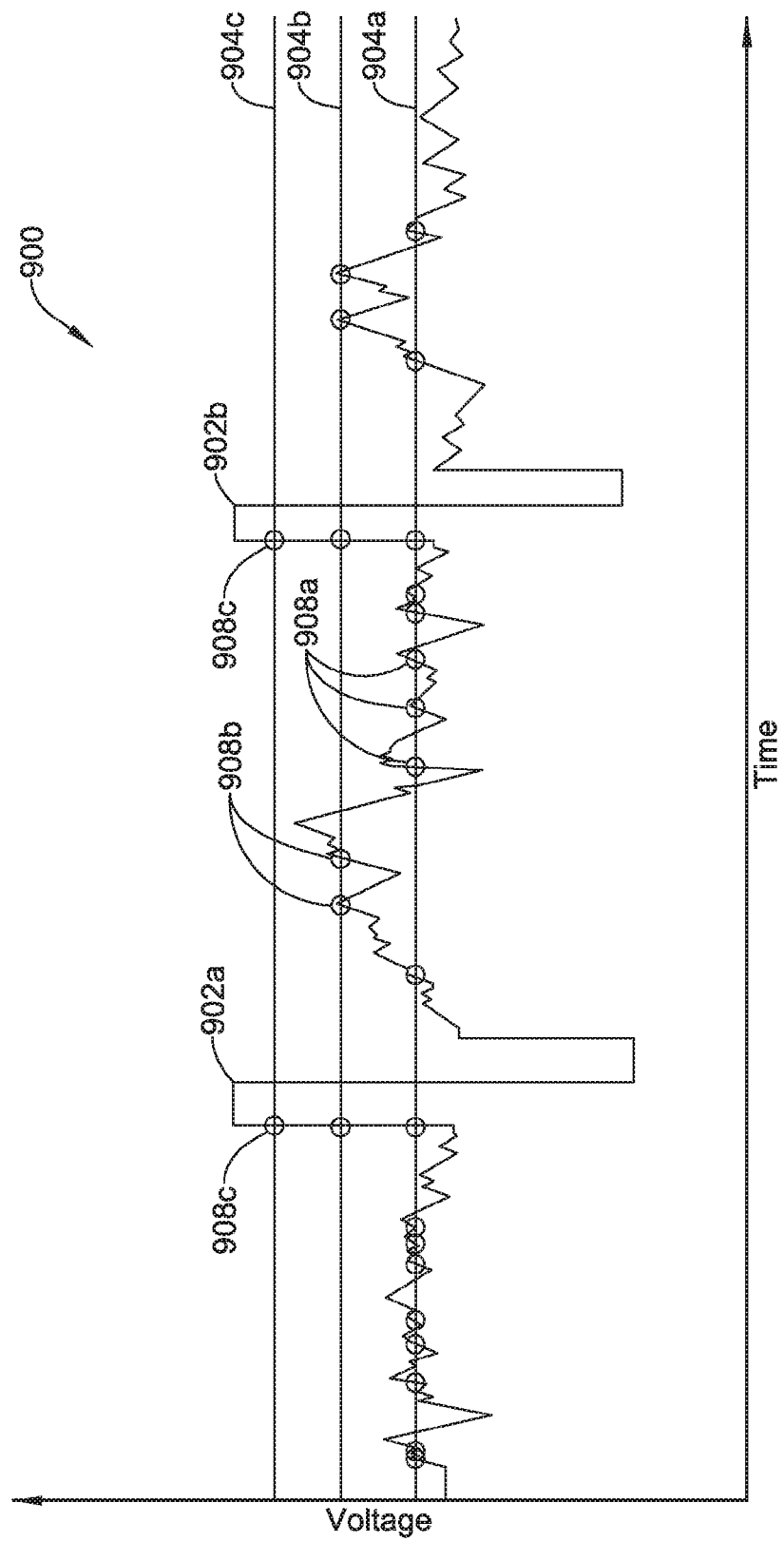
FIG. 9 is a graphical representation of an example sensed signal including communication pulses and noise signals, in accordance with an example of the present disclosure.

The above description is just one example of how an MCRT test may operate. In other examples, instead of beginning with a relatively low voltage threshold 604, LCP 402 may begin with a relatively high voltage threshold and, for subsequent MCRT tests, may reduce the voltage threshold. In such examples, LCP 402 may identify the lowest tested voltage threshold for which the number of delivered pulses and detected crossings of the voltage threshold were acceptable and set the MCRT for future communications equal to that threshold (sometimes plus a margin). In still other examples, LCP 402 may perform one MCRT test, but evaluate the results using differing thresholds. This example is depicted by FIG. 9. As can be seen in FIG. 9, the single MCRT test results in a single signal 900, including pulses 902a-b. LCP 402 may analyze signal 900 using multiple voltage thresholds 904a-c. For each voltage threshold, LCP 402 may count the number of crossings from below the voltage thresholds to above the voltage thresholds, as indicated by markers 908a-c.

In some examples, an MCRT test may include a timing aspect in addition to a threshold aspect. In MCRT tests which employ only a threshold aspect, there could be situations where a voltage level of a delivered pulse falls below the voltage threshold, but the voltage level of a noise or other signal rises above the voltage threshold. In such situations, the receiving device may erroneously end up counting a number of received pulses equal to the number of delivered pulses. In order to combat against this type of error, the delivering device may be configured to deliver pulses at predetermined times or at a predetermined frequency. In such examples, the receiving device may only count the number of crossings of the voltage threshold if they occurred at the predetermined times or at the end of predetermined intervals (determined by the predetermined frequency). In additional examples, the receiving device may employ a window around the predetermined times or end of predetermined intervals. The receiving device may the threshold crossings only if they occur within the windows.

Figure 10:
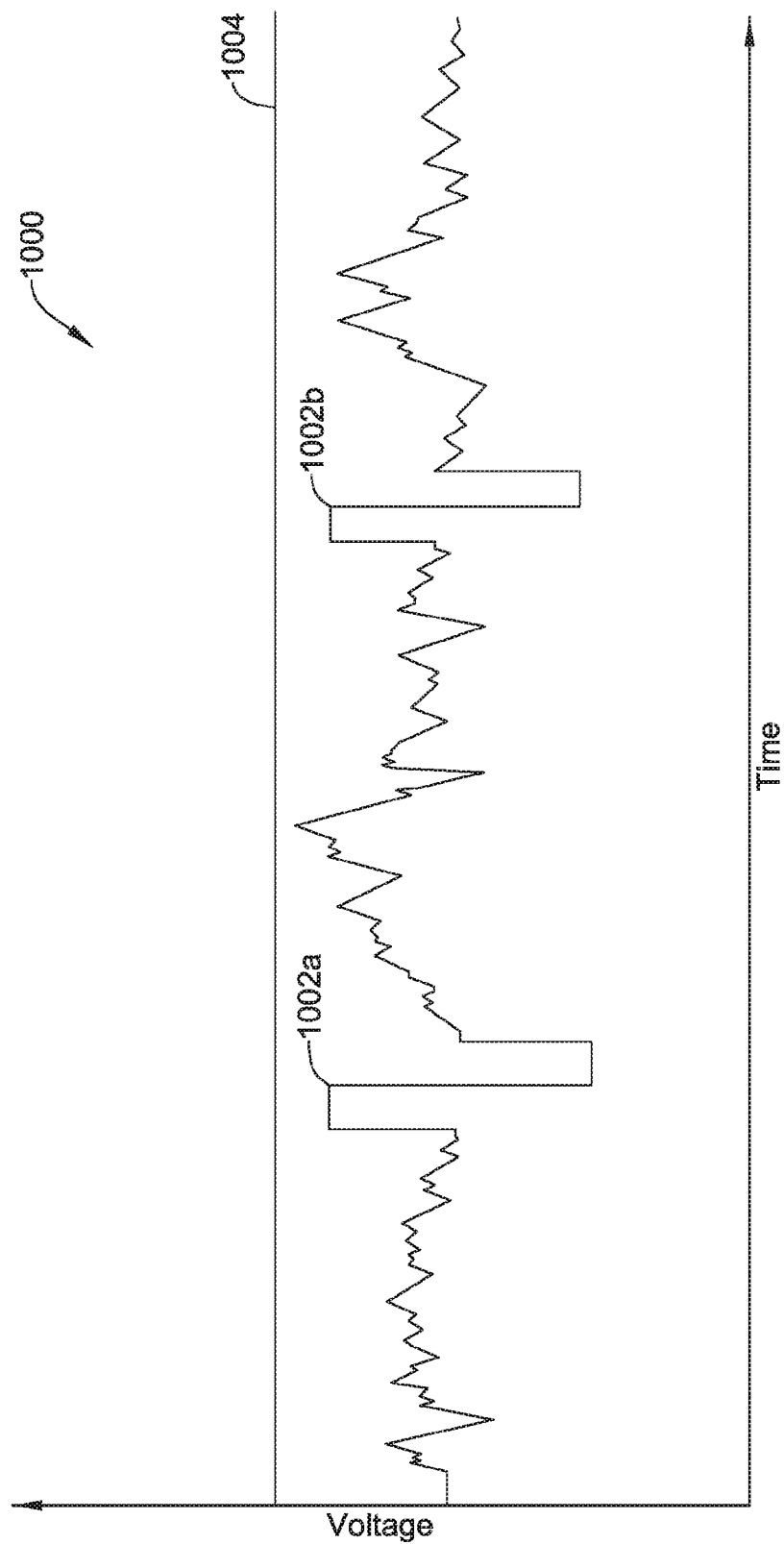
FIG. 10 is a graphical representation of an example sensed signal including communication pulses and noise signals, in accordance with an example of the present disclosure.
Figure 11:
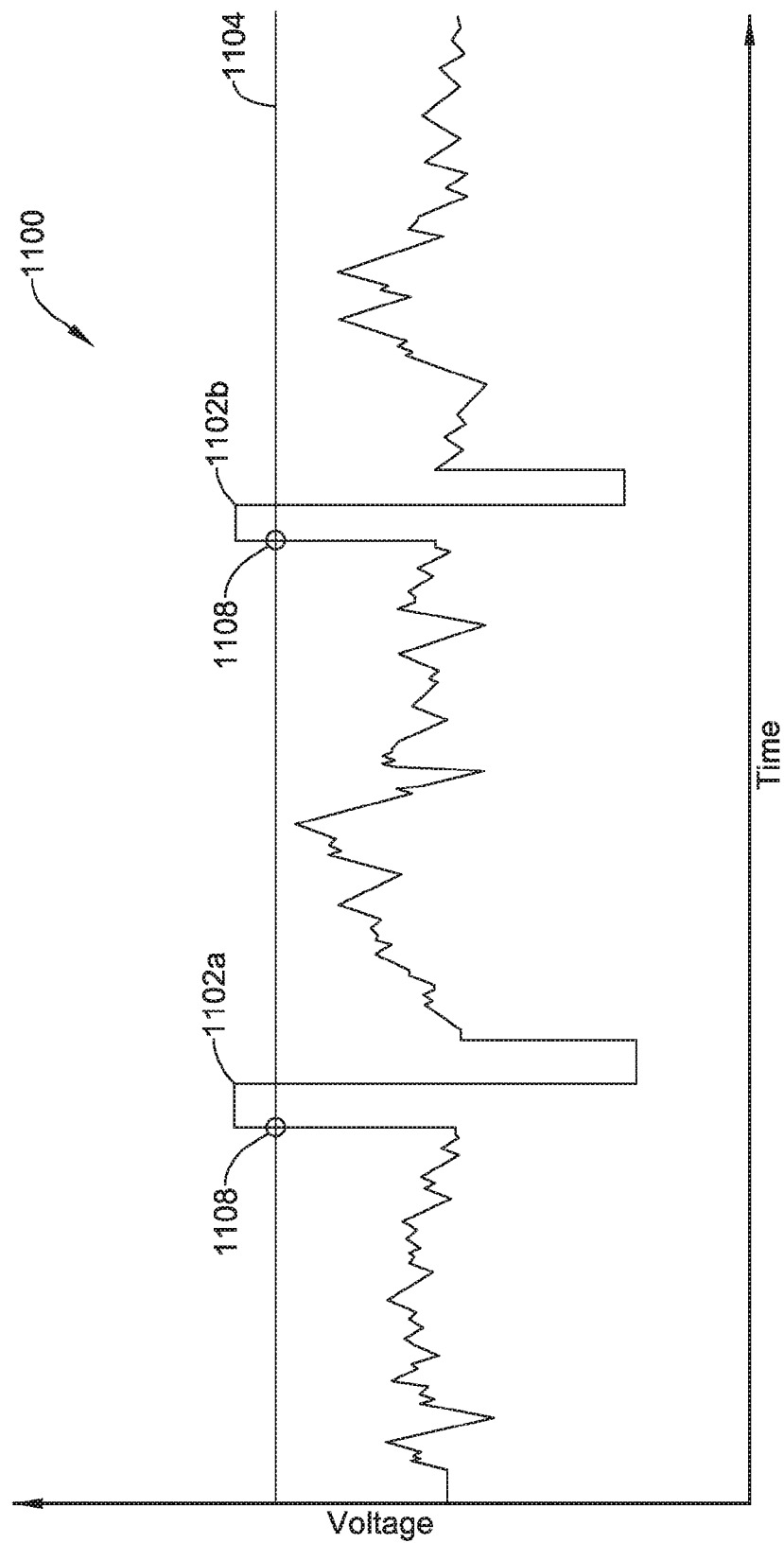
FIG. 11 is a graphical representation of an example sensed signal including communication pulses and noise signals, in accordance with an example of the present disclosure.

FIGS. 10 and 11 illustrate an additional feature of at least some MCRT tests. FIG. 10 depicts signal 1000, including pulses 1002a-b. As can be seen in FIG. 10, LCP 402 would be unable to set voltage threshold 1004 at a value such that only pulses 1002a-b would rise above voltage threshold 1004. In these examples, LCP 402 may be unable to determine a voltage threshold where the number of detected crossings of the voltage threshold is acceptable. LCP 402 may then send a communication to the S-ICD requesting that the S-ICD increase the energy level of the delivered pulses. In this particular example, this means that the S-ICD would increase the voltage amplitude of the delivered pulses. In other examples, the S-ICD may increase the pulse width, the electrical power of the pulses, the electrical energy of the pulses, or some other parameter. FIG. 11 depicts signal 1100, including communication pulses 1102a-b. In the example of FIG. 11, the S-ICD has increased the energy level of the delivered communication pulses 1102a-b (e.g. increased the voltage amplitude). Now, pulses 1102a-b do cross from below voltage threshold 1104 to above voltage threshold 1104, as represented by markers 1108. LCP 402 may then proceed to determine a MCRT. Additionally in such examples, aside from LCP 402 setting a MCRT for future communications, the S-ICD may also change the energy level of delivered communication pulses for future communications. The MCRT may be set above the noise level by an amount that produces a desired signal-to-noise (SN) ratio.

In some cases, an MCRT test may be repeated multiple times with the same voltage threshold to help confirm the results. If the number of signal crossings from below the voltage thresholds to above the voltage thresholds changes with each repeated MCRT test, then a maximum count value, an average count value, a mean count value or any other suitable value may be used to determine if the number of delivered pulses acceptably matches the detected crossings of the voltage threshold. In some cases, a standard deviation of the number of signal crossings may be calculated across multiple MCRT tests using the same voltage threshold, and if the standard deviation is above a threshold deviation, the MCRT test may be deemed to have failed and the voltage threshold may be increased. This is just one example.

Although the above MCRT test descriptions are illustrated with respect to LCP 402, each device of a medical device system may have its own MCRT. Accordingly, each device of a system may independently determine an MCRT. In some cases, LCP 402 may determine a different MCRT for each medical device that provides pulses to the LCP 402. For example, LCP 402 may determine a first MCRT for pulses provided by an S-ICD, a second MCRT for pulses provided by another LCP, and a third MCRT for pulses provided by a diagnostic only sensor device. This is just an example.

Devices of a medical system may adjust other aspects of communication in order to achieve energy usage reduction. For example, a device, such as LCP 402 and/or the S-ICD, may adjust the energy level of communication pulses used during communication. As part of an MCRT test, or separate from an MCRT test, a device may periodically perform a communication pulse Energy Level Reduction test (ELRT). Typical periods between performing such ELRT tests may include once a day, once a week, once a month, or any other suitable period of time. In other examples, a device may perform such a ELRT test based on trigger events, for example upon detection of a threshold amount of ignored communication attempts, temperature changes, voltage changes, or delivery of one or more therapies. For instance, a first device may send communication pulses to a second device which would normally cause the second device to response with one or more communication pulses. The first device may count a number of times that the first device has issued a communication without receiving a response from the second device. After the count reaches a threshold amount, the first device may trigger the second device to perform a communication pulse ELRT test. In such examples, the first device may communicate the trigger to the second device using an alternative communication method, or the first device may adjust one or more parameters of the communication pulses (e.g. raise the voltage amplitude to a high level) before communicating the trigger to the second device. In addition to the foregoing, and in some cases, a trigger event may include other events such as a change in a device parameter (e.g. pacing rate), a change in a patients activity (change in hemodynamic demand), a change in a patients posture, a detected patient event (e.g. defibrillation shock), a change in a communication parameter (e.g. frequency). A device may perform a communication pulse ELRT test, at implant, periodically and/or upon trigger events.

Figure 12:
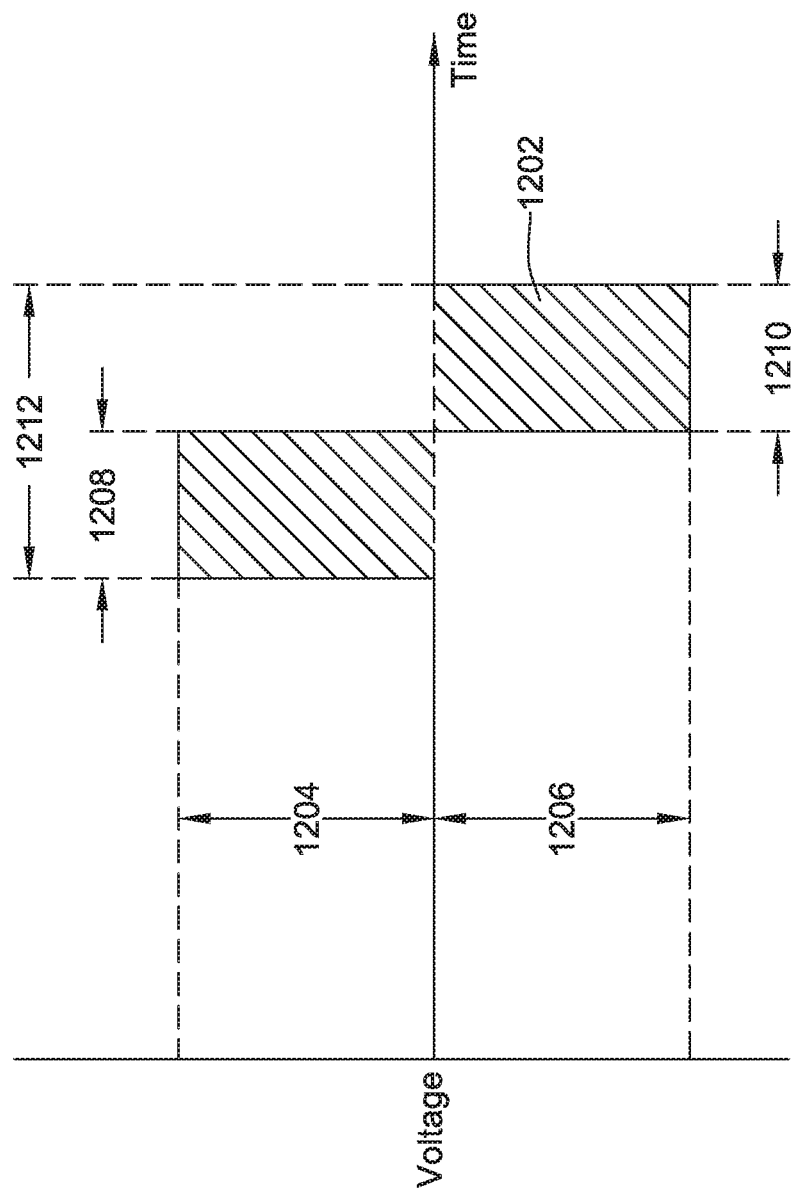
FIG. 12 is a graphical representation of an example communication pulse, in accordance with an example of the present disclosure.

FIG. 12 is an illustration of an example communication pulse, including various features of the communication pulse. In the example of FIG. 12, communication pulse 1202 is a biphasic communication pulse with positive polarity voltage amplitude 1204, negative polarity voltage amplitude 1206, positive pulse width 1208, negative pulse width 1210, and total pulse width 1212. Communication pulse 1002 should be construed only as one example of a communication pulse that a device may employ. Other example communication pulses may be monophasic, either positive polarity or negative polarity, and have any suitable morphology. Additionally, in at least some examples, there may be a time period between positive pulse width 1208 and negative pulse width 1210, if desired.

Communication pulse 1202 may have a total energy level, and the total energy level of communication pulse 1202 may be related to parameters of communication pulse 1202 such as the amplitudes, pulse widths, and morphology (or shape) of communication pulse 1202. For simplicity, the described examples may focus on changing the energy of communication pulse 1202 by changing the amplitude and/or pulse width or communication pulse 1202, but in other examples, the energy level of communication pulse 1202 may be changed by changing the morphology of communication pulse 1202, or even the specific vector by which the delivering device delivers communication pulse 1202.

When a device, such as LCP 402 or the S-ICD, delivers a communication pulse, the communication pulse will have a first energy level at the time of delivery. When conducted communication is used, as the communication pulse travels through tissue of the patient, the communication pulse will attenuate and arrive at a receiving device with a second lower energy level. Accordingly, a delivering device needs to ensure that the energy level of the communication pulse at the time of delivery is great enough such that when the communication pulse arrives at the receiving device, the communication pulse still has sufficient energy for the receiving device to recognize the communication pulse as a communication pulse and distinguish it from noise. In the examples of FIGS. 6-9, this would mean the communication pulses would need to have a voltage level above the MCRT of the receiving device. However, if the delivering device delivers communication pulses with a higher energy level than the MCRT of the receiving device, the delivering device may be using more stored energy than is required—as generating the communication pulses consumes energy that is typically stored in a limited energy source such as a battery or other energy storage module. Accordingly, by performing a communication pulse ELRT test, a device may reduce the amount of energy used during communications by lowering the amount of energy used for to generate the communication pulses.

A device, for example LCP 402, may begin a communication pulse ELRT test by delivering pulses with relatively high energy levels. The delivered pulses may be communication pulses, such as depicted with respect to FIG. 12, or test pulses which have similar features to communication pulse 1202 but may not convey information to the receiving device. In the example of FIG. 12, this may mean that LCP 402 may deliver a first sequence of one or more pulses 1202 during a predetermined time period, where the pulses have relatively high positive polarity voltage amplitude 1204 and/or negative polarity voltage amplitude 1206. The receiving device, for example the S-ICD, may count a number of signals that the S-ICD determined as communication pulses during the predetermined time period (for example, by noting the number of signals which crossed an energy or other threshold). The predetermined period of time may be a portion of the cardiac cycle between heartbeats—e.g. after a T-wave but before a subsequent P-wave. In other examples, the predetermined period of time may span multiple cardiac cycles. For instance, the predetermined period of time may include multiple non-consecutive periods of time, wherein each period of time is the portion of the cardiac cycle between heartbeats.

In the communication pulse ELRT test, LCP 402, similar to the S-ICD as described above with respect to MCRT tests, may be configured to deliver a set amount of pulses at regular intervals or at random intervals during the predetermined time period. Alternatively, LCP 402 may be configured to deliver a random or bounded-random number of pulses either at regular or irregular intervals during the predetermined time period. In some cases, the protocol by which LCP 402 delivers pulses during the communication pulse energy level reduction test is also known to the S-ICD. Accordingly, the S-ICD may know the timing and/or number of pulses that LCP 402 delivers during the communication pulse ELRT test. Alternatively, LCP 402 may send a separate communication after the communication pulse ELRT test to the S-ICD indicating the number of pulses LCP 402 delivered during the communication pulse ELRT test.

If the number of delivered pulses and the number of pulses identified by the S-ICD are acceptable, LCP 402 and the S-ICD may repeat the communication pulse ELRT test, with LCP 402 delivering pulses with lower energy levels. As described, the energy level of the pulses may be related to a positive polarity voltage amplitude, for instance positive polarity voltage amplitude 1204 of communication pulse 1202, a negative polarity voltage amplitude, for instance negative polarity voltage amplitude 1206 of communication pulse 1202, and a pulse width, such as pulse widths 1208 and 1210 (or total pulse width 1212) of communication pulse 1202. Accordingly, in order to produce pulses with lower energy levels, LCP 402 may reduce the positive polarity voltage amplitude of the delivered pulses, the negative polarity voltage amplitude of the delivered pulses, the pulse widths of the pulses, or any combination of these parameters. LCP 402 and the S-ICD may repeat this process until the number of delivered pulses and the number of pulses identified by the S-ICD are unacceptable. Once the numbers become unacceptable, LCP 402 may set the energy level of communication pulses for use in future communication equal to the lowest energy level for which the numbers were acceptable (sometimes plus a margin). For example, LCP 402 may generate communication pulses during future communications with parameters equal to the parameters of delivered pulses that had the lowest energy level for which the numbers were acceptable (sometimes plus a margin). If, during the initial sequence of the test, the numbers were unacceptable, then instead of repeating the process after lowering the energy level of the delivered pulses, LCP 402 may instead raise the energy level of the delivered pulses. In such circumstances, it may be the case that the initial energy level of the delivered pulses was not high enough to meet the MCRT of the S-ICD.

Of course, the above description of the communication pulse ELRT test is only one way in which LCP 402 and the S-ICD may perform a communication pulse ELRT test. In other examples, LCP 402 may begin a communication pulse energy level reduction test by delivering pulses with relatively low energy levels. If the number of delivered pulses and the number of pulses identified by the S-ICD are initially unacceptable, then LCP 402 may increase the energy level of the pulses and repeat a delivery sequence.

As noted above, a communication pulse ELRT tests may include adding a safety margin to the energy levels of communication pulses used for future communications. For example, the attenuation of delivered communication pulses may change as a function of the respiratory cycle of a patient or other biological processes. Accordingly, it is possible that even after LCP 402 determines an energy level of communication pulses for use in future communications, delivering communication pulses with that energy level may not reach the energy level of the S-ICD's MCRT. In order to account for this variability, LCP 402 may add a safety margin to the energy level of communication pulses determined based on the communication pulse ELRT test. For example, LCP 402 may use communication pulses for future communications with energy levels five percent, ten percent, fifteen percent, twenty percent, or any other suitable percentage level higher than the energy level determined by the communication pulse ELRT test.

The above example was described from the perspective of setting an energy level for communication pulses for use in communications by LCP 402. In some examples, each device of a medical device system may perform a similar test to set an energy level for communication pulses for future communications. However, each communication pulse ELRT test may determine an appropriate energy level for communication pulses for use in communication between a pair of devices. For example, the amount of energy a communication pulse has when it arrives at a device may be a function of the distance between the delivering device and the receiving device, the type of tissue between the devices, the respiratory cycle of the patient, and other biological or other factors. Accordingly, a communication pulse delivered by a single device may arrive at multiple different devices with differing energy levels. Each device, then, may perform a MCRT and/or communication pulse ELRT test with respect to each other device of the system. Each test may determine an energy level of communication pulses for use in communications between each delivering device/receiving device pair. In some examples, each device may store the results of each test, e.g. an association between a specific device and an energy level of communication pulses. Then, when a device communicates information to another device, the delivering device may deliver communication pulses with the energy level associated with the receiving device that it has stored in memory. If a device communicates simultaneously with multiple devices, the delivering device may use communication pulses with an energy level that is the highest of the energy levels associated with the receiving devices. In other examples, a device may only store the highest energy level of communication pulses after performing a communication pulse energy level reduction test for each other device in the system. This may reduce an amount of memory required for storing energy level associations while ensuring that a delivering device can communicate with each other device of the system.

Some medical device systems may employ both MCRT tests and communication pulse ELRT tests. In these systems, the devices may first perform an MCRT test to determine an appropriate minimum communication receive threshold (MCRT). Setting the MCRT to an appropriate level first establishes a floor for communication pulse energy levels. In some cases, these MCRT tests may be performed at implant, at scheduled times, in response to detected trigger events, and/or at any other suitable times. After the MCRT tests, the devices of the system may perform communication pulse ELRT tests. These communication pulse ELRT tests may establish an energy level of delivered communication pulses such that the energy level of the delivered communication pulses received at the receiving device may be close to, but still above, the MCRT of the receiving device.

In some additional or alternative examples, a device may employ a maximum energy threshold test. A maximum energy threshold test (MELT) may establish a maximum energy level of communication pulses that a device may be configured to deliver. The maximum energy threshold may be an energy level threshold where delivering communication pulses with energy levels above the maximum energy threshold may cause unwanted stimulation of the patient (e.g. capture of the heart, stimulation of muscles, stimulation of nerves, etc.). As with the other tests, a device may periodically perform a MELT test. Typical periods between performing a MELT test may include once a day, once a week, once a month, or any other suitable period of time. In other examples, a device may perform a MELT test based on trigger events, for example upon detection of a threshold amount of cardiac capture events caused by delivered communication pulses, after delivery of a defibrillation pulse, after delivery of ATP therapy, after a detected threshold change in the amount of energy currently stored in an energy storage module, or after a detected threshold change in temperature. For instance, a device delivering communication pulses may monitor for whether the delivered communication pulses capture the heart. Upon detection of a threshold amount of capture events, the device may perform a MELT test. In other examples, other devices may monitor for capture events and communicate a trigger to the device that delivered the communication pulses after detecting a threshold amount of capture events. In addition to the foregoing, and in some cases, a trigger event may include other events such as a change in a device parameter (e.g. pacing rate), a change in a patients activity (change in hemodynamic demand), a change in a patients posture, a detected patient event (e.g. defibrillation shock), a change in a communication parameter (e.g. frequency). In some cases, a device may perform a MELT test at implant, periodically and/or upon trigger events.

In some examples, one or more of the devices may monitor for an evoked response in order to determine whether the heart was captured by one or more communication pulses. Alternatively, or in addition, one or more of the devices may monitor for a loss of, or delayed, intrinsic event. Other methods for determining whether the heart was captured can be found in U.S. Provisional Patent Application No. 62/034,494, filed on Aug. 7, 2014, entitled "Medical Device Systems and Methods with Multiple Communication Modes," the entirety of which is incorporated herein by reference. If, based on the disclosed one or more methods, the device determines that communication pulses delivered by the device captured the heart, then the device may perform a MELT test.

While capture of the heart is used here as an example of unwanted stimulation, it is contemplated that unwanted stimulation may include any suitable unwanted stimulation event, such as unwanted nerve or muscle stimulation. For example, an accelerometer or the like in LCP 402 may be used to detect movement of the diaphragm or unwanted hiccupping caused by unwanted stimulation of the phrenic nerve by communication pulses. In such examples, movement of the accelerometer in a time window after delivering a communication pulse may be indicative of unwanted stimulation—as the unwanted nerve or muscle stimulation may cause LCP 402, and accordingly the accelerometer, to move.

Figure 13:
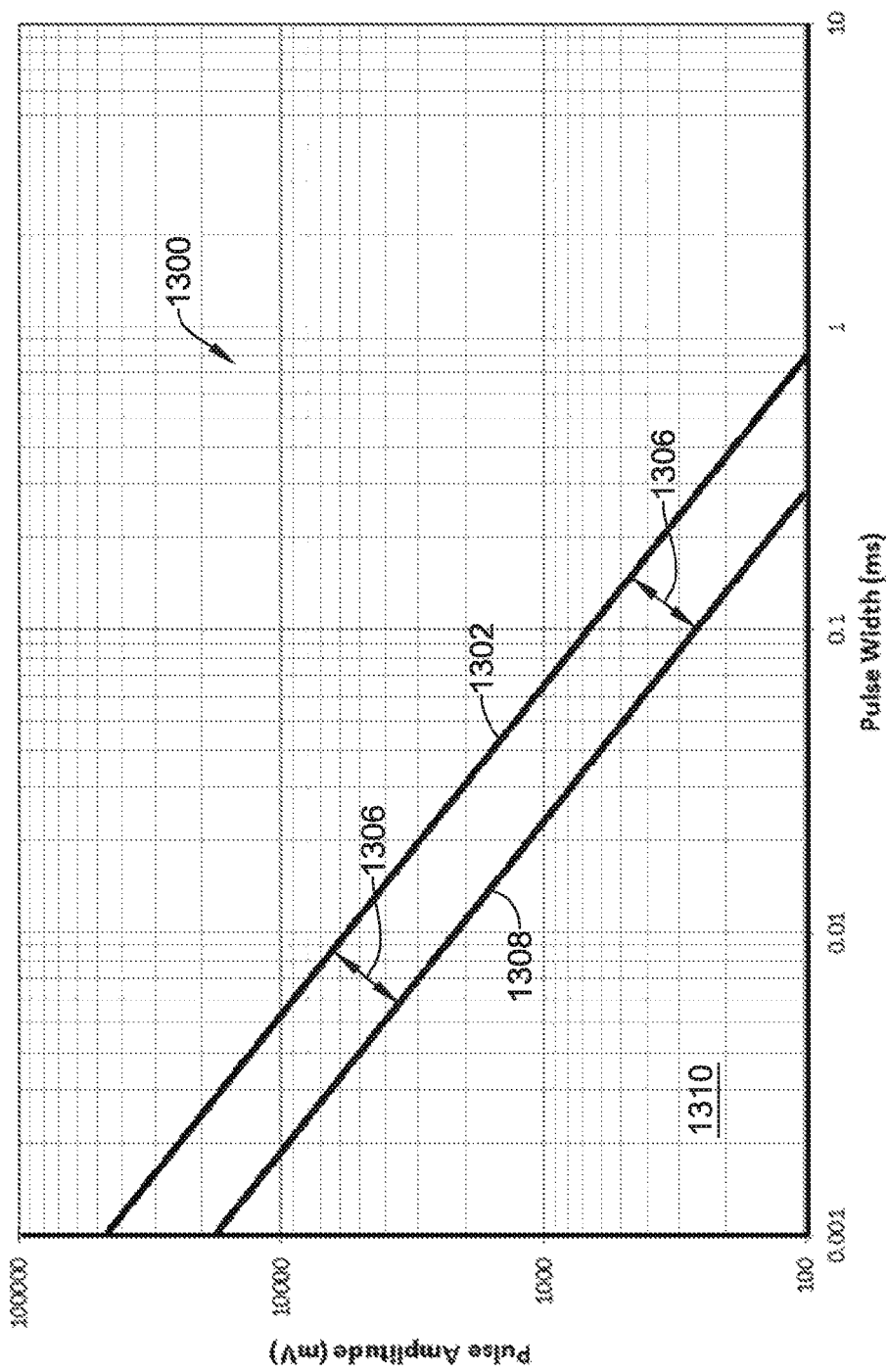
FIG. 13 is a graphical representation of a strength-duration curve, in accordance with an example of the present disclosure.

In performing a MELT test, a device, such as LCP 402 or the S-ICD, may determine multiple combinations of parameters for pulses (e.g. communication pulses or test pulses) which result in capture of the heart, thereby determining multiple capture thresholds for the heart. Using the determined multiple combinations of parameters, LCP 402 may determine a curve or function representative of combinations of parameters which resulted in capture of the heart, for example by using one or more regression techniques. Continuing the examples described in FIGS. 6-9, LCP 402 may use conducted pulses, where the energy level of the pulses may be related to the voltage amplitude and the pulse width parameters of the pulses. FIG. 13, then, is a graph of pulse amplitude vs. pulse width in millivolts and milliseconds, and includes an illustrative example of what such a curve or function may look like. Curve 1302 represents combinations of parameters of pulses which may result in capture of the heart—e.g. curve 1302 may represent a capture threshold curve. Curve 1302 additionally represents a dividing line between combinations of parameters of conducted pulses which, when delivered to tissues of a patient, would result in capture of the patient's heart and those that would not result in capture of the patient's heart. For instance, any combinations of pulse amplitudes and pulse widths that lie on curve 1302 or above and to the right of curve 1302 would result in capture. Any combinations of pulse amplitudes and pulse widths that lie below and to the left of curve 1302 would not result in capture. This region is defined as safe zone 1310.

In some examples, LCP 402 may determine a shifted curve related to curve 1302 by a safety margin. The shifted curve is represented by curve 1308. In such examples, safe zone 1310 may be the combinations of pulse amplitudes and pulse widths that lie below and to the left of shifted curve 1308. The amount LCP 402 shifts curve 1302 is represented by safety margin 1306. Safety margin 1306 may represent an amount such that if curve 1302 changes as a function of time or other factors, curve 1302 will not, or is statistically unlikely to, drift below and to the left of curve 1308. Curve 1308 may be considered the maximum energy threshold for LCP 402. LCP 402 may be configured to not deliver conducted communication pulses with combinations of parameters that lie on curve 1308 or above and to the right of curve 1308. In some examples, curve 1302 and/or curve 1308 may be considered unwanted stimulation thresholds.

During a MELT test, LCP 402 may deliver communication pulses to tissue of the patient that cause capture of the heart. Accordingly, in some MELT tests during periods where LCP 402 is currently providing electrical stimulation therapy, LCP 402 may deliver communication pulses in lieu of pacing pulses. If LCP 402 determines that a delivered communication pulse did not cause capture of the heart, for example by detecting a lack of an evoked response in a time period succeeding the delivered communication pulse, LCP 402 may then deliver a safety pacing pulse. The safety pacing pulse, which may be similar to a pacing pulse, is designed to ensure capture of the heart occurs. In this manner, LCP 402 may save energy by employing communication pulses to capture the heart of the patient and only employing additional pulses, e.g. safety pacing pulses, if the delivered communication pulses failed to capture the heart, rather than delivering both communication pulses and pacing pulses. Additionally, by only employing safety communication pulses, LCP 402 may avoid an issue with causing multiple captures of the heart from both the communication pulses and the pacing pulses.

In examples where LCP 402 determines a maximum energy threshold, LCP 402 may additionally compare the maximum energy threshold to the energy levels determined based on communication pulse energy level reduction tests. For instance, in the example of FIG. 12, LCP 402 determined values of one or more voltage amplitude parameters and/or values of one or more pulse width parameters of communication pulses that LCP 402 may deliver to tissue of the patient when communicating with other devices. If LCP 402 determines that one or more of the determined combinations of parameters for the communication pulses lie on or is above and to the right of curve 1308, LCP 402 may take one or more actions. For instance, LCP 402 may cease delivering communication pulses for communication with any device for which the associated one or more voltage amplitude parameters and/or one or more pulse width parameters lie on or above and to the right of curve 1308. In other examples, LCP 402 may enter a safety communication mode, such as described in U.S. Provisional Patent Application No. 62/034,494, filed on Aug. 7, 2014, entitled "Medical Device Systems and Methods with Multiple Communication Modes", which may limit the communication functionality of LCP 402. When in the normal communication mode, LCP 402 may be configured to deliver communication pulses within one or more first communication windows during each cardiac cycle. In the safety communication mode, LCP 402 may be configured to deliver communication pulses within one or more second communication windows during each cardiac cycle. The one or more second communication windows may be shorter than the one or more first communication windows. Alternatively, or additionally, the one or more second communication windows may occur at different times within a cardiac cycle than the one or more first communication windows.

Additionally, or alternatively, any the above described examples may include performing the disclosed tests for each available vector of the device. In some examples, one or more devices of a system may be able to deliver and/or receive communication pulses via different vectors, where a vector is a combination of at least two electrodes. A vector may comprise two of any of combination of implanted, percutaneous, or transcutaneous electrodes that are found on a device. For instance, a device may include more than two electrodes and may accordingly deliver and/or receive communication pulses via different combinations of the electrodes. Each available receiving vector for a device may receive different levels of noise or other signals. Additionally, the energy level of a communication pulse or the level of attenuation of the communication pulse may be affected by the specific vector via which a device delivers the communication pulse. Accordingly, in some examples a device may perform an MCRT test, a ELR test, or a MELT test for each available vector of the device. The device may then select an appropriate receiving vector and an appropriate delivering vector. The appropriate receiving vector may be the vector with the lowest MCRT value. The appropriate delivering vector may be the vector for which the device determined communication pulses for future communication use that had the lowest energy level out of all the determined communication pulses for all of the other vectors. In some ELR test examples, selecting a receiving vector and/or a delivering vector may occur instead of adjusting any of the parameters of the communication pulses.

Figure 14:
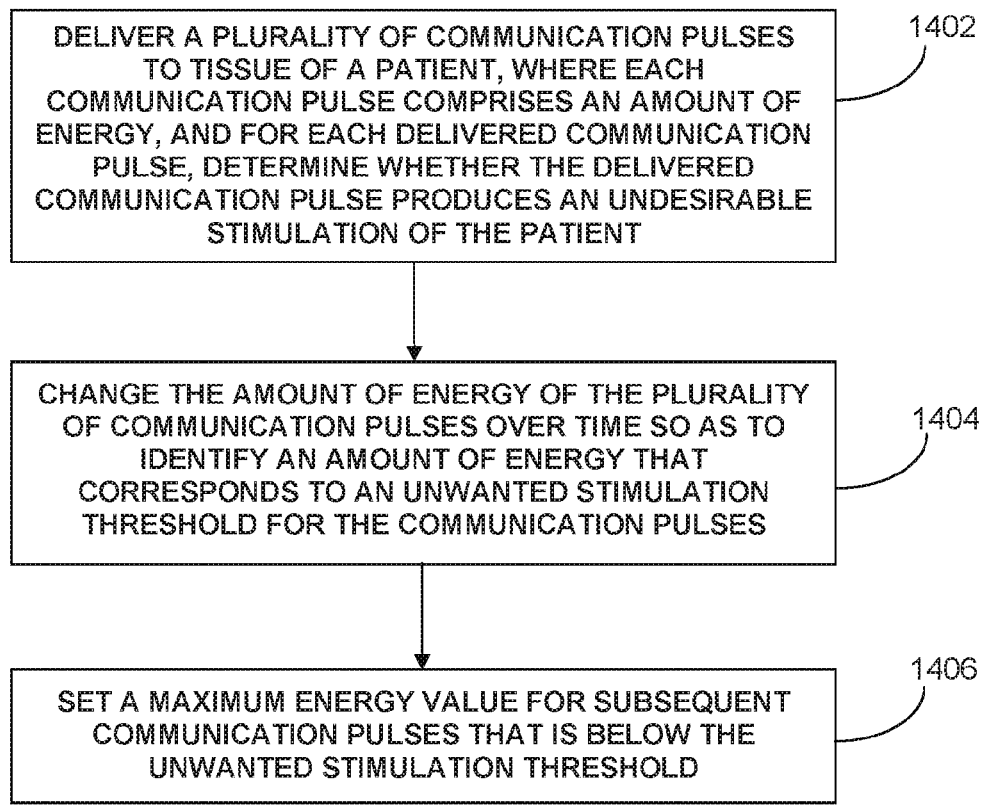
FIG. 14 is a flow diagram of an illustrative method that may be implemented by a medical device or medical device system, such as the illustrative medical devices and medical device systems described with respect to FIGS. 1-2 and 4-5.

FIG. 14 is a flow diagram of an illustrative method that may be implemented by an implantable medical device, such as shown in FIGS. 1 and 2, or a medical device system such as shown in FIGS. 4 and 5. Although the method of FIG. 14 will be described with respect to LCP 100 and an S-ICD, the illustrative method of FIG. 14 may be performed using any suitable medical devices or medical device systems. FIG. 14 shows one illustrative MELT test.

According to the method depicted in FIG. 14, a medical device may be implanted within a patient, such as if the medical device is an LCP, ICP, an ICD, an S-ICD, or may be disposed in proximity to the patient, such as if the medical device is an external medical device. The medical device may be configured to deliver a plurality of communication pulses to tissue of the patient, where each communication pulse includes an amount of energy, and for each delivered communication pulse, it may be determined whether the delivered communication pulse produces an unwanted stimulation of the patient, as shown at 1402. In some cases, the medical device that delivered the communication pulses may determine whether the delivered communication pulse produces an unwanted stimulation of the patient. In other cases, another medical device, such as the receiving medical device or some other medical device (e.g. accelerometer, acoustic sensor, etc.) may determine whether the delivered communication pulse produces an unwanted stimulation of the patient. The medical device may change the amount of energy of the plurality of communication pulses over time so that an amount of energy that corresponds to an unwanted stimulation threshold for the communication pulses can be identified, as shown at 1404. The medical device may then set a maximum energy value for subsequent communication pulses that is below the identified unwanted stimulation threshold, as shown at 1406.

Figure 15:
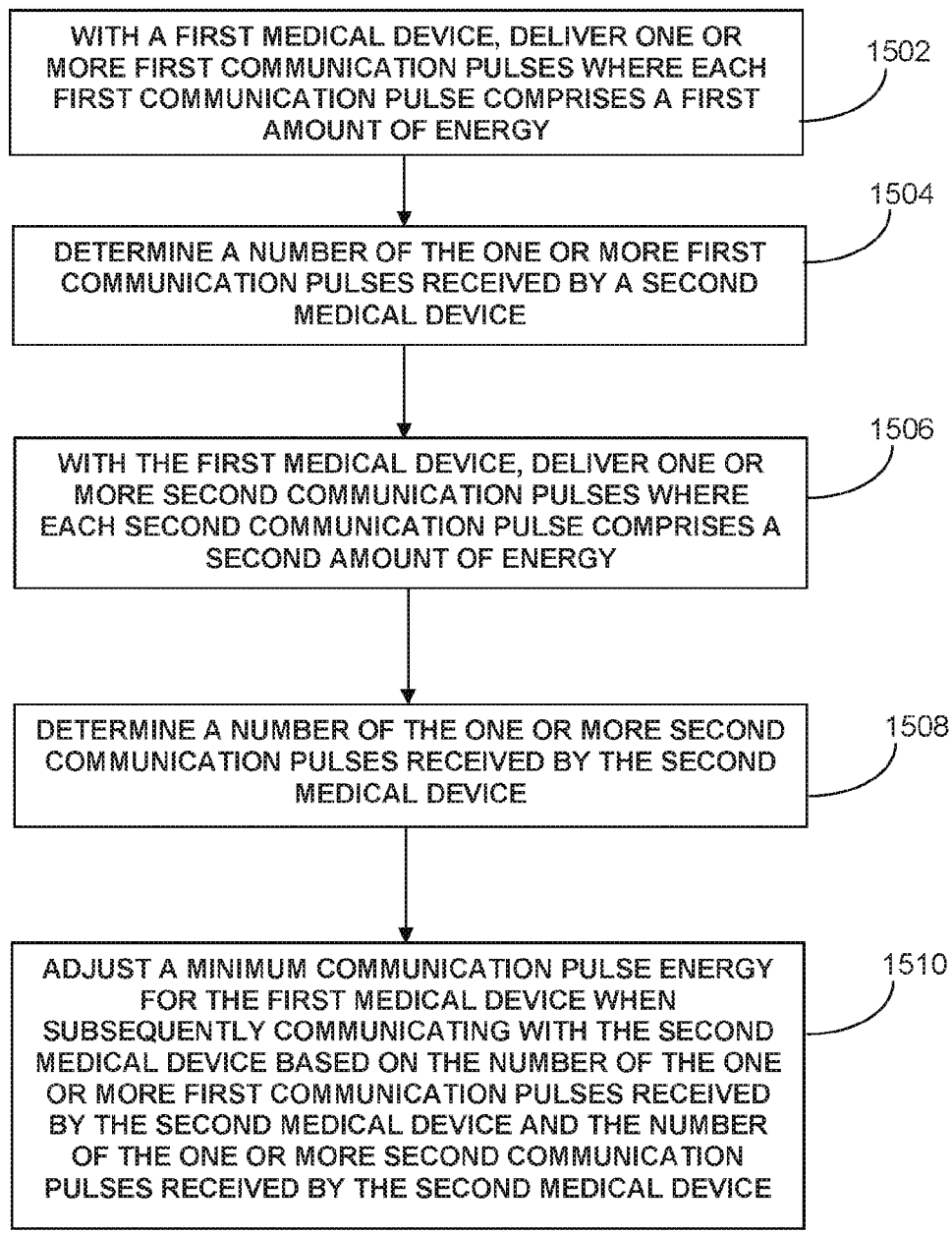
FIG. 15 is a flow diagram of an illustrative method that may be implemented by a medical device or medical device system, such as the illustrative medical devices and medical device systems described with respect to FIGS. 1-2 and 4-5.

FIG. 15 is a flow diagram of an illustrative method that may be implemented by an implantable medical device, such as shown in FIGS. 1 and 2, or a medical device system such as shown in FIGS. 4 and 5. Although the method of FIG. 15 will be described with respect to LCP 100 and an S-ICD, the illustrative method of FIG. 15 may be performed using any suitable medical devices or medical device systems.

According to the illustrative method depicted in FIG. 15, a first medical device may be implanted within a patient, such as if the first medical device is an ICP, an ICD, an S-ICD, or may be disposed in proximity to the patient, such as if the first medical device is an external medical device. The first medical device may be part of a medical device system along with a second medical device, such as LCP 100. In such a medical device system, a first medical device may deliver one or more first communication pulses where each first communication pulse includes a first amount of energy, as shown at 1502. The second medical device may then determine a number of the one or more first communication pulses received by the second medical device, as shown at 1504. The first medical device may then deliver one or more second communication pulses where each second communication pulse includes a second amount of energy, as shown at 1506. The second medical device may then determine a number of the one or more second communication pulses received by the second medical device, as shown at 1508. Finally, the first medical device may adjust a minimum communication pulse energy for when the first medical device subsequently communicates with the second medical device based on the number of the one or more first communication pulses received by the second medical device and the number of the one or more second communication pulses received by the second medical device, as shown at 1510. Of course in other examples, LCP 100 may be the first medical device, and the second medical device may be any of an ICP, an ICD, an S-ICD, or an external medical device.

Figure 16:
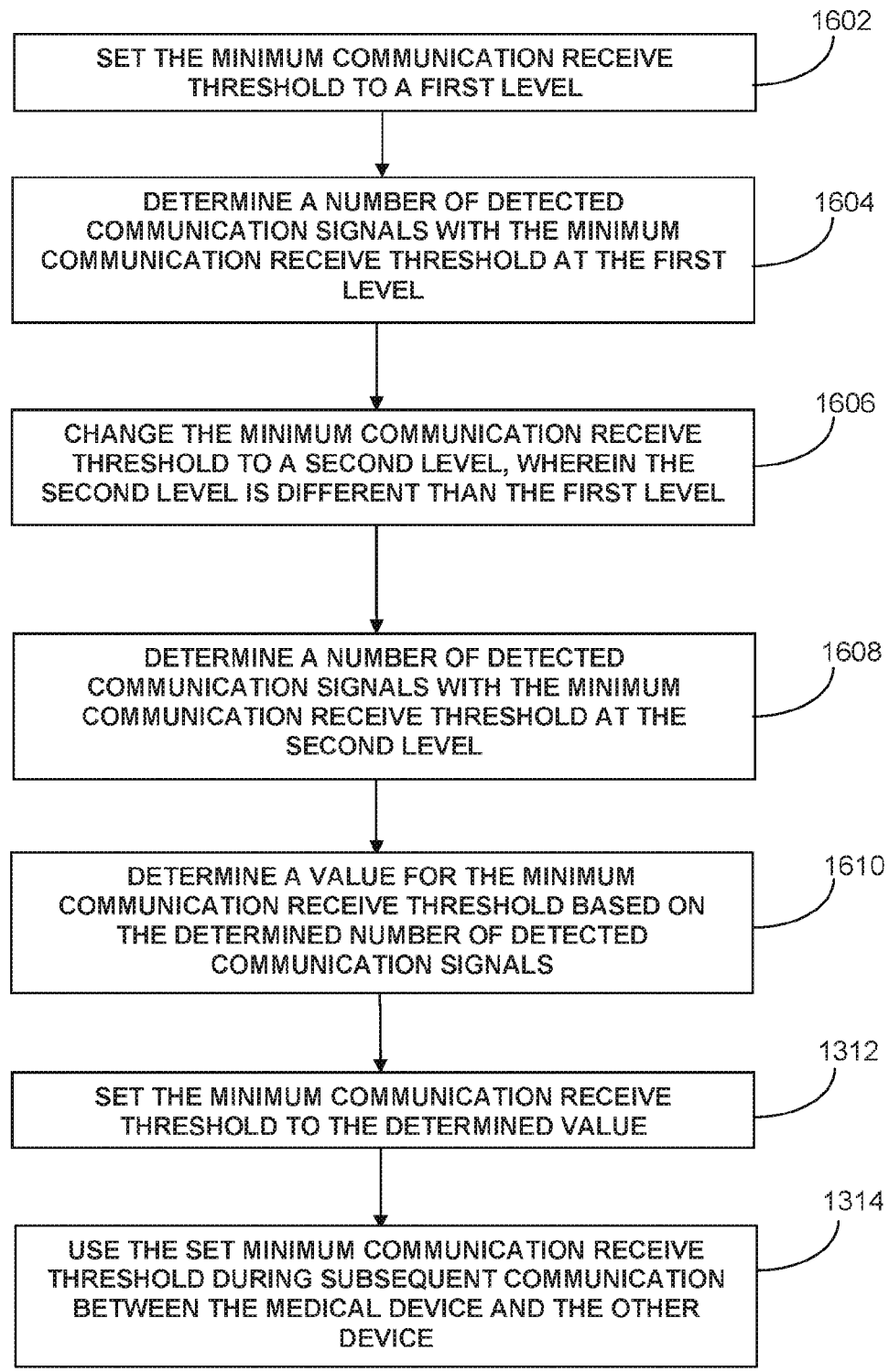
FIG. 16 is a flow diagram of an illustrative method that may be implemented by a medical device or medical device system, such as the illustrative medical devices and medical device systems described with respect to FIGS. 1-2 and 4-5.

FIG. 16 is a flow diagram of an illustrative method that may be implemented by an implantable medical device, such as shown in FIGS. 1 and 2, or a medical device system such as shown in FIGS. 4 and 5. Although the method of FIG. 16 will be described with respect to LCP 100 and an S-ICD, the illustrative method of FIG. 16 may be performed using any suitable medical devices or medical device systems.

According to the illustrative method depicted in FIG. 16, a medical device may be implanted within a patient, such as if the first medical device is an LCP, ICP, an ICD, an S-ICD, or may be disposed in proximity to the patient, such as if the first medical device is an external medical device. The medical device may operate to determine a minimum receive threshold for use when receiving communication signals from another device. For example, the medical device may set the minimum communication receive threshold to a first level, as shown at 1602. The medical device may then determine a number of detected communication signals with the minimum communication receive threshold at the first level, as shown at 1604. The communication signals may, for example, be delivered by another device to tissue of the patient and for reception by the medical device. The other medical device may be, for example, an LCP, ICP, ICD, S-ICD, or an external medical device. The medical device may then change the minimum communication receive threshold to a second level, wherein the second level is different than the first level, as shown at 1606. Then, the medical device may determine a number of detected communication signals with the minimum communication receive threshold at the second level, as shown at 1608. Again, the communication signals may be delivered by the other medical device. The medical device then determines a value for the minimum communication receive threshold based on the determined number of detected communication signals, as shown at 1610. Finally, the medical device may set the minimum communication receive threshold to the determined value, as shown at 1612, and use the set minimum communication receive threshold during subsequent communication between the medical device and the other medical device, as shown at 1614.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed:

1. A method for setting an energy level for communication pulses of a medical device, the method comprising:
   delivering a plurality of pulses to tissue of a patient, where each pulse includes an amount of energy, and for each delivered pulse, determining whether the delivered pulse produces an unwanted stimulation of the patient;
   changing the amount of energy of the plurality of pulses over time so as to identify an amount of energy that corresponds to an unwanted stimulation threshold for the pulses;
   setting a maximum energy value for communication pulses that is below the unwanted stimulation threshold; and
   delivering communication pulses to tissue of the patient at or below the maximum energy value during communication with another device.

2. The method of claim 1, wherein the maximum energy value is set a predetermined safety margin below the unwanted stimulation threshold.

3. The method of claim 1, wherein the unwanted stimulation is a capture of a heart of the patient.

4. The method of claim 3, wherein delivering the plurality of pulses to tissue of the patient comprises delivering a pulse in lieu of a pacing pulse, and delivering a safety pacing pulse if the pulse did not capture the heart.

5. The method of claim 1, wherein the unwanted stimulation is a stimulation of a nerve of the patient.

6. The method of claim 1, wherein the unwanted stimulation is a stimulation of a muscle of the patient.

7. The method of claim 1, wherein the amount of energy of each pulse is defined at least in part by an amplitude, a pulse width, a morphology, and/or a specific vector via which the pulse is delivered.

8. The method of claim 1, further comprising repeating the delivering, changing and setting steps from time to time.

9. The method of claim 1, further comprising repeating the delivering, changing and setting steps in response to a trigger event.

10. The method of claim 9, wherein the trigger event comprises a detected reduction in reliability and/or accuracy of the communication with the other device.

11. A medical device comprising:
   a communication module configured to deliver a plurality of communication pulses to tissue of a patient in order to communicate with another device, where each communication pulse comprises an amount of energy;
   a control module operatively coupled to the communication module, the control module configured to detect a reduction in reliability and/or accuracy of communication with the other device, and if a reduction in reliability and/or accuracy is detected, the control module is configured to:
- identify an amount of energy that corresponds to an unwanted stimulation threshold for the communication pulses;
- set a maximum energy value for the communication pulses that is below the unwanted stimulation threshold; and
- deliver communication pulses below the maximum energy value during subsequent communication with the other device.

12. The medical device of claim 11, wherein the control module is further configured to detect an unwanted stimulation of the patient by a communication pulse, and if an unwanted stimulation of the patient is detected, the control module is further configured to:
- identify an amount of energy that corresponds to an unwanted stimulation threshold for the communication pulses;
- set a maximum energy value for communication pulses that is below the unwanted stimulation threshold; and
- deliver communication pulses below the maximum energy value during subsequent communication with the other device.

13. The medical device of claim 11, wherein the maximum energy value is set a predetermined safety margin below the unwanted stimulation threshold.

14. The medical device of claim 11, wherein the amount of energy of each communication pulse is defined at least in part by an amplitude, a pulse width, a morphology, and/or a specific vector via which the communication pulse is delivered.

15. The medical device of claim 11, wherein the unwanted stimulation of the patient comprises a capture of a heart of the patient.

16. The medical device of claim 11, wherein the unwanted stimulation of the patient comprises a stimulation of a nerve of the patient.

17. The medical device of claim 11, wherein the unwanted stimulation of the patient comprises a stimulation of a muscle of the patient.

18. A medical device comprising:
- a communication module configured to deliver a plurality of communication pulses to tissue of a patient in order to communicate with another device, where each communication pulse comprises an amount of energy;
- a control module operatively coupled to the communication module, the control module configured to detect an unwanted stimulation of the patient, and if an unwanted stimulation of the patient is detected, the control module is configured to:
  - identify an amount of energy that corresponds to an unwanted stimulation threshold for the communication pulses;
  - set a maximum energy value for communication pulses that is below the unwanted stimulation threshold; and
  - deliver communication pulses below the maximum energy value during subsequent communication with the other device.

19. The medical device of claim 18, wherein the maximum energy value is set a predetermined safety margin below the unwanted stimulation threshold.

20. The medical device of claim 18, wherein the unwanted stimulation of the patient comprises a capture of a heart of the patient.

* * * * *